(12) United States Patent
Edenhofer et al.

(10) Patent No.: US 8,481,492 B2
(45) Date of Patent: Jul. 9, 2013

(54) FUSION PROTEIN AND USE THEREOF

(75) Inventors: Frank Edenhofer, Erftstadt (DE);
Manal Hadenfeld, Cologne (DE);
Michael Peitz, Bonn (DE);
Marc-Christian Thier,
Bad-Munstereifel (DE)

(73) Assignee: Life & Brain GmbH, Bonn (DE)

( * ) Notice: Subject to any disclaimer, the term of this patent is extended or adjusted under 35 U.S.C. 154(b) by 134 days.

(21) Appl. No.: 12/997,659

(22) PCT Filed: Jun. 15, 2009

(86) PCT No.: PCT/EP2009/004287
§ 371 (c)(1),
(2), (4) Date: Apr. 6, 2011

(87) PCT Pub. No.: WO2009/149956
PCT Pub. Date: Dec. 17, 2009

(65) Prior Publication Data
US 2011/0177557 A1 Jul. 21, 2011

(30) Foreign Application Priority Data
Jun. 13, 2008 (EP) .................................. 08010805

(51) Int. Cl.
*A61K 38/00* (2006.01)
*C07K 1/00* (2006.01)

(52) U.S. Cl.
USPC .......................................... 514/16.5; 530/350

(58) Field of Classification Search
USPC .......................................... 530/350; 514/16.5
See application file for complete search history.

(56) References Cited

FOREIGN PATENT DOCUMENTS

| | | |
|---|---|---|
| JP | 2005-110565 A | 4/2005 |
| WO | WO 2006/113181 A2 | 10/2006 |
| WO | WO 2008/105630 A1 | 9/2008 |
| WO | WO 2009/032456 A2 | 3/2009 |
| WO | WO 2009/067757 A1 | 6/2009 |

OTHER PUBLICATIONS

Krosl et al., Nature Medicine, 9(11), 1428-1432, 2003.*
Bosnali Manal, et. al.; "Generation of transducible versions of transcription factors Oct4 and Sox2", Biological Chemistry, Walter De Gruyter GMBH & Co., Berlin, DE, vol. 389, No. 7, Jul. 1, 2008, pp. 851-861, XP009118395; ISSN: 1431-6730.
Heng Boon Chin, et al., "Induced Pluripotent Stem Cells (iPSC)—can direct delivery of transcription factors into the cytosol overcome the perils of permanent genetic modification?", Minimally Invasive Therapy & Allied Technologies: Official Journal of the Society for Minimally Invasive Therapy; Mitat, Informa Healthcare, London, vol. 17, No. 5, Jan. 1, 2008, pp. 326-328, XP009118397; ISSN: 1365-2931.
J. Krosl, et al., "In vitro expansion of hematopoietic stem cells by recombinant TAT-HOXB4 protein", Nature Medicine, Nature Publishing Group, New York, NY, vol. 9, No. 11, Nov. 1, 2003, pp. 1428-1432, XP003016542, ISSN: 1078-8956.
Landry, Josette-Renée, et al., "Runx genes are direct targets of Scl/Tal1 in the yolk sac and fetal liver.", Blood, Mar. 15, 2008, vol. 111, No. 6, pp. 3005-3014, XP002545673; ISSN: 0006-4971.
Bian Jing, et al., "Effect of cell-based intercellular delivery of transcription factor GATA4 on ischemic cardiomyopathy.", Circulation Research, Jun. 8, 2007, vol. 100, No. 11, pp. 1626-1633, XP002545674, ISSN: 1524-4571.
Heng B C, et al., "Incorporating protein transduction domains (PTD) within intracellular proteins associated with the 'stemness' phenotype. Novel use of such recombinant 'fusion' proteins to overcome current limitations of applying autologous adult stem cells in regenerative medicine?", Medical Hypotheses, Eden Press, Penrith, US, vol. 64, No. 5, Jan. 1, 2005, pp. 992-996, XP004952000, ISSN: 0306-9877.
Heng B C, et al., "Incorporating protein transduction domains (PTD) within recombinant 'fusion' transcription factors. A novel strategy for directing stem cell differentiation?", Biomedicine and Pharmacotherapy, Elsevier, Paris, FR, vol. 59, No. 3, Apr. 1, 2005; pp. 132-134, XP004861305, ISSN: 0753-3322.

* cited by examiner

*Primary Examiner* — Maryam Monshipouri
(74) *Attorney, Agent, or Firm* — Faegre Baker Daniels LLP

(57) ABSTRACT

The invention relates to a fusion protein and a method for the generation of the fusion protein of the invention. Further, the invention relates to the use of the fusion protein of the invention for the generation of induced pluripotent cells. Moreover, the invention relates to a composition comprising at least one fusion protein of the invention.

18 Claims, 19 Drawing Sheets

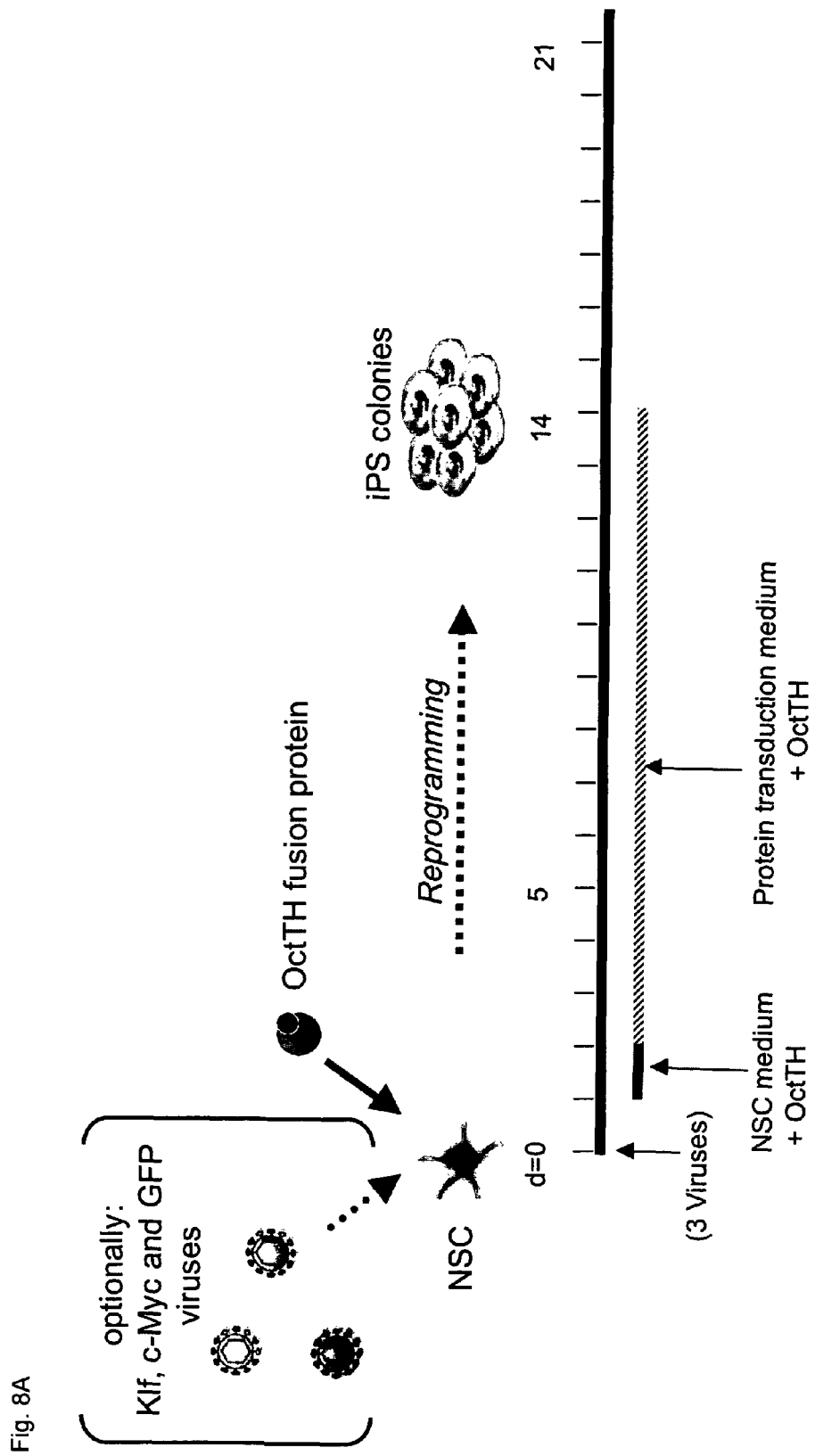

FUSION PROTEIN AND USE THEREOF

CROSS-REFERENCE TO RELATED APPLICATION

Figures 1A, 1B:
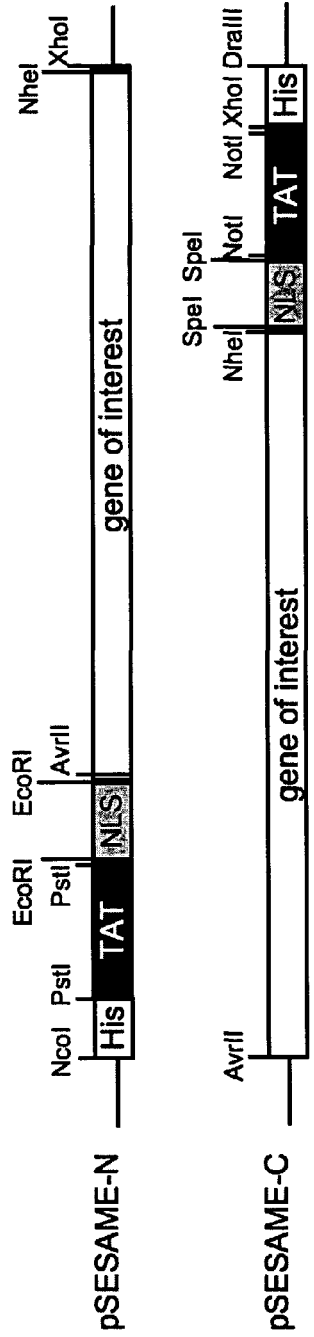

This application is a National Stage filing of International Application Serial No. PCT/EP2009/004287, filed Jun. 15, 2009 and designating the United States, which claims priority to European Patent Application No. 08010805.3 filed Jun. 13, 2008, the disclosures of which are expressly incorporated herein by reference.

FIELD OF THE INVENTION

The invention relates to a fusion protein and a method for the generation of the fusion protein of the invention. Further, the invention relates to the use of the fusion protein of the invention for the generation of induced pluripotent cells. Moreover, the invention relates to a composition comparison at least one fusion protein of the invention.

BACKGROUND OF THE INVENTION AND STATE OF THE ART

Toward the end of the last century, the remarkable conjunction of the discoveries of mammalian cloning and human embryonic stem (ES) cells almost immediately gave rise to speculation that the fusion of these technologies might be used to generate customized pluripotent stem cell lines from individual patients (Wilmut (1998)). ES cells have the unique potential to differentiate into cell types of the three germ layers and the capacity of unlimited self renewal (Smith, 2001). Such cell lines could therefore help to overcome the formidable hurdle of immune rejection of transplants derived from allogeneic ES cells, and could also provide laboratory models for the study of complex human diseases. Proof of concept for this approach in the mouse was not long in coming (Munsie et al. (2000)), but ethical and practical barriers have slowed extension of somatic cell nuclear transfer to the human.

Although it was obvious that reprogramming of somatic cells by cloning or cell fusion (Tada et al. (1997)) must involve gene-factors present specifically in the egg or in pluripotent stem cells, both processes seemed highly complex, and the list of factors involved was potentially quite long. Yamanaka's landmark study (Takahashi&Yamanaka (2006)) was striking because it reduced the reprogramming process to the action of a few genes. Soon, the same group, and several others, showed that induced pluripotent stem (iPS) cells produced by modifications of the original method had identical properties to those of pluripotent stem cell lines derived from embryos (Okita et al. (2007) and Wernig et al. (2007)). However, chimeric mice derived from these cell lines still developed tumors, the formation of which was linked causally to use of the c-myc gene in the reprogramming protocol.

During the last years various studies were reported aiming at deciphering the molecular mechanisms that promote the exclusive properties of ES cells. Cytokines such as leukemia inhibitory factor (LIF) and bone morphogenic protein (BMP) turned out to be sufficient to maintain pluripotency of ES cells. Moreover, internal regulatory pathways consisting of a self-organized transcription factor network appear to play an essential role in the regulation of early embryonic development (for review see Niwa, 2007). In this respect the transcription factors Oct4, Sox2 and Nanog seem to form a core network for the regulation of pluripotency (Boyer et al., 2005; Loh et al., 2006). In addition epigenetic processes such as bivalent chromatin domains and polycomb group proteins are fundamental for the maintenance of pluripotency (Bernstein et al., 2006; Boyer et al., 2006).

A major breakthrough in stem cell research was the recently reported successful reprogramming of murine fibroblasts to induced pluripotent stem (iPS) cells (Takahashi et al., 2006; Okita et al., 2007; Wernig et al., 2007; Maherali et al., 2007). It turned out that four factors, namely Oct4, Sox2, Klf4 and cMyc are particularly capable of establishing pluripotency in somatic cells. The same factors were shown to be able to reprogram human somatic cells to iPS cells (Takahashi et al., 2007; Lowry et al., 2008). More recently it has been reported that cMyc is dispensable for reprogramming (Park et al., 2007; Nakagawa et al., 2008; Wernig et al., 2008). Thomson and co-workers showed that reprogramming of human ES cells is possible by another combination of factors which is Oct4, Sox2, Nanog and LIN28, whereas Oct4 and Sox2 were indispensable for this process in comparison to the other two factors (Yu et al., 2007).

Oct4 is a POU-domain transcription factor (encoded by Pou5f1) that is expressed in all blastomers of early developing embryos and later during embryonic development it is restricted to the inner cell mass (ICM). It is down regulated in trophectodermal and primitive endodermal tissues (Nichols et al., 1998; Niwa et al., 2000). RNAi interference (RNAi) knock down of Pou5f1 in murine ES cells results in differentiation (Hay et al., 2004; Hough et al., 2006). At maturity, Oct4 expression is exclusive to developing germ cells (Pesce and Scholer, 2001).

Sox2 is a member of the SRY-related HMG box transcription factor family, and exhibits a similar expression pattern to Oct4 in early embryonic development. Sox2 interacts with Oct4 to regulate pluripotency and segregation to the first three lineages (Avilion et al., 2003). A knock down of Sox2 by RNAi causes differentiation to multiple lineages including trophectoderm (Ivanova et al., 2006). Interestingly, a composite POU-HMG DNA-binding site was found to be conserved in the regulatory region of many developmental genes. The regulation of these genes by the interaction of POU homeodomain and HMG factors is thought to be a fundamental mechanism for the regulation of expression of developmental genes (Dailey & Basilico, 2001). Oct4 and Sox2 act cooperatively to activate the expression of several pluripotency factors such as Fgf4, Utf1, Fbx15, Nanog (Boyer et al., 2005; Loh et al., 2006) (Kuroda et al., 2005; Nishimoto et al., 1999; Rodda et al., 2005; Tokuzawa et al., 2003; Yuan et al., 1995) and additionally regulate the expression of their own genes (Chew et al., 2005; Okumura-Nakanishi et al., 2005; Tomioka et al., 2002).

So far all studies investigating the influence of particular transcription factors, such as Sox2 and Oct4, on reprogramming of adult stem cells to iPS cells were based on genetic modification. However, random integration of transgene sequences into the genome can cause insertional mutagenesis (Glover et al., 2005; Okita et al., 2007) which limits later therapeutically use immensely. Further, the forced transgene expression known within the state of the art (e.g. DNA transfection or viral transduction) is elaborate and expensive.

Therefore, there is a need for a method for the generation of induced pluripotent cells which do not involve genetic modification.

The inventors of the present invention devised that induced pluripotent cells can be generated by transduction of a particular fusion protein into adult (stem) cells.

SUMMARY OF THE INVENTION

In a first aspect the present invention relates to a fusion protein comprising a) a protein transduction domain (PTD) comprising 6 to 12 basic amino acids; and b) at least one transcription factor.

In a second aspect the present invention relates to a fusion protein comprising: a) at least one transcription factor, wherein between 6 to 12 amino acids of said transcription factor have been replaced by basic amino acids.

In a third aspect the present invention relates to a use of the fusion protein according to the first or the second aspect for the generation of induced pluripotent cells or for the differentiation of pluripotent cells.

In a fourth aspect the present invention relates to a composition containing at least one fusion protein according to the first or the second aspect and at least one stabilizer.

In a fifth aspect the present invention relates to a method for generating the fusion protein according to the first or the second aspect comprising the steps: a) constructing a DNA sequence comprising a sequence encoding a PTD and a sequence encoding a transduction factor; b) cloning the DNA sequence into a suitable vector; c) transforming the vector in a suitable expression system; and d) optionally purifying the expressed fusion proteins.

In a sixth aspect the present invention relates to a nucleic acid comprising a nucleotide sequence encoding the fusion protein as defined in the first or the second aspect.

In a seventh aspect the present invention relates to a method for generating induced pluripotent cells, comprising the step: a) contacting at least one fusion protein as defined in the first or the second aspect with at least one target cell.

In an eighth aspect the present invention relates to a method for generating induced pluripotent cells, comprising the steps: a) carrying out steps a) to c) of the method according to the fifth aspect, wherein step c) of the fifth aspect is carried out in a cell-free expression system; and b) contacting the cell-free expression system of step a) with at least one target cell.

This summary of the invention does not necessarily describe all features of the invention.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

"Protein transduction" is a recently developed method that is able to circumvent genetic modification. A transducible protein can be directly applied to target cells due to fusion to a so-called protein transduction domain (PTD) (also referred to as cell penetrating peptide, CPP), which promotes the translocation of the protein into the cells (Dietz and Bahr, 2004; Joliot and Prochiantz, 2004; Kaplan et al., 2005). We previously demonstrated that the protein transduction technique can be applied to various proteins including site specific recombinases (Peitz et al., 2002; Nolden et al., 2006) and eukaryotic transcription factors (Landry et al., 2008).

A "transcription factor" (sometimes called a sequence-specific DNA binding factor) is a protein that binds to specific parts of DNA using DNA binding domains and is part of the system that controls the transfer (or transcription) of genetic information from DNA to RNA. Transcription factors perform this function alone, or by using other proteins in a complex, by increasing (as an activator), or preventing (as a repressor) the presence of RNA polymerase, the enzyme which activates the transcription of genetic information from DNA to RNA. Transcription factors are modular in structure and contain the following domains:

(1) DNA-binding domain (DBD) which attach to specific sequences of DNA (enhancer or promoter sequences) adjacent to regulated genes. DNA sequences which bind transcription factors are often referred to as response elements.

(2) Trans-activating domain (TAD) which contain binding sites for other proteins such as transcription coregulators. These binding sites are frequently referred to as activation functions (AFs).

(3) An optional signal sensing domain (SSD) (e.g., a ligand binding domain) which senses external signals and in response transmit these signals to the rest of the transcription complex resulting in up or down regulation of gene expression. Alternatively the DBD and signal sensing domains may reside on separate proteins that associate within the transcription complex to regulate gene expression.

Within the present invention any transcription factor can be used which is known to a person skilled in the art as suitable for the purpose of the present invention.

As used herein, a "domain" is a discrete portion of a protein with its own function.

A "protein transduction domain" (PTD) is any domain which is able to mediate the penetration of the fusion protein of the present invention into a target cell. Within the present invention, the PTD preferably comprises 6-12 basic amino acids. Functional assays to determine whether a protein domain is capable to act as a protein transduction domain are known to the person skilled in the art. For example, the potential PTD may be expressed in a fusion protein fused to another protein that yields a detectable signal, e.g. a fluorescent signal, such as green fluorescent protein and variants thereof. This fusion protein can be contacted with one or more target cells and the penetration of the fusion protein into the target cells can be monitored by using a microscope. In another assay the potential PTD may be labeled with a detectable label, such as a fluorescent label. The penetration of the detectably labeled PTD into a target cell can again be monitored by using a microscope. If the fusion protein comprising the potential PTD or the detectably labeled, potential PTD penetrates into the target cell, said domain is a protein transduction domain.

A "nuclear localizing sequence" is an amino acid sequence which acts like a 'tag' on the exposed surface of a protein. This sequence is used to target the protein to the cell nucleus through the Nuclear Pore Complex and to direct a newly synthesized protein into the nucleus via its recognition by cytosolic nuclear transport receptors. Typically, this signal consists of one or more short sequences of positively charged lysines or arginines. Different nuclear localized proteins may share the same NLS. An NLS has the opposite function of a nuclear export signal, which targets proteins out of the nucleus. Functional assays to determine whether a protein domain is capable of acting as a nuclear localizing sequence are known to the person skilled in the art. For example, a protein that yields a detectable signal, e.g. a fluorescent signal, such as green fluorescent protein and variants thereof, may be expressed within a cell. In one experiment, said protein is expressed without the potential NLS. In another experiment, said protein is expressed in a fusion protein with the potential NLS. The subcellular localization of the proteins can be observed by using a microscope. If the fusion protein comprising the potential NLS is present in the nucleus to a higher degree as compared the protein lacking the potential NLS, the potential NLS is indeed capable of acting as an NLS.

"Oct4" is a POU-domain transcription factor (encoded by Pou5f1) that is expressed in all blastomers of early developing embryos and later during embryonic development it is restricted to the inner cell mass (ICM). It is down regulated in trophectodermal and primitive endodermal tissues. RNAi interference (RNAi) knock down of Pou5f1 in murine ES cells results in differentiation. At maturity, Oct4 expression is exclusive to developing germ cells.

"Sox2" is a member of the SRY-related HMG box transcription factor family, and exhibits a similar expression pattern to Oct4 in early embryonic development. Sox2 interacts with Oct4 to regulate pluripotency and segregation to the first three lineages.

Stem Cells: In contrast to primary cells, stem cells can serve as a potentially unlimited source for the isolation of differentiated specific cell types (Poulsom R. et al., 2002; Gepstein L. 2002). Stem cells in the context of this invention refer to cells having the ability to both regenerate, i.e. being able to proliferate while still maintaining their stem cell characteristics, and to develop via a process known as "differentiation" to one or more specialized cell types, for example, cardiac muscle cells, endothelial cells, cartilage cells, bone cells, fat cells, neuronal cells, hepatocytes or insulin producing cells (Wobus A M. Mol Aspects Med. 2001 June; 22(3): 149-64).

"Cellular differentiation" is a process by which a less specialized cell becomes a more specialized cell type.

As used herein, the term "somatic cells" refers to cells that are able to undergo maturation or have already matured to one or more tissue-specific cell types. Somatic cells have the capacity to develop into numerous types of tissues, for example, bone, dental bone, cartilage, tendons, bone marrow stroma, neural tissue, skin, pancreas, liver, fat tissue, and muscle.

As used herein, the term protein "variant" is to be understood as a polypeptide which differs in comparison to the polypeptide which is derived by one or more changes in the amino acid sequence. The polypeptide from which a variant is derived is also known as the parent polypeptide. Typically a variant is constructed artificially, preferably by gene-technological means. Typically, the polypeptide from which the variant is derived is a wild-type protein or wild-type protein domain. However, the variants usable in the present invention may also be derived from homologs, orthologs, or paralogs of the parent polypeptide or from artificially constructed variants, provided that the variant exhibits at least one biological activity of the parent polypeptide. The changes in the amino acid sequence may be amino acid exchanges, insertions, deletions, N-terminal truncations, or C-terminal truncations, or any combination of these changes, which may occur at one or several sites. The amino acid exchanges may be conservative or non-conservative. In preferred embodiments, a variant usable in the present invention differs from the protein or domain from which it is derived at least by 1, 2, 3, 4, 5, 6, 7, 8, 9, 10, 15, 20, 25, 30, 35, 40, 45, 50, 55, 60, 65, 70, 75, 80, 85, 90, 95, 100 or more amino acid exchanges, preferably conservative amino acid changes. Variants may additionally or alternatively comprise deletions of amino acids, which may be N-terminal truncations, C-terminal truncations or internal deletions or any combination of these. Such a deletion variant may be naturally occurring (e.g. splice variants) or it may be constructed artificially, preferably by gene-technological means. Typically, the protein or protein domain from which the deletion variant is derived is a wild-type protein. However, the variants of the present invention carrying deletions may also be derived from homologs, orthologs, or paralogs of the parent polypeptide or from artificially constructed variants, provided that the deletion variants exhibit at least one biological activity of the parent polypeptide. Preferably a variant has a deletion of 1, 2, 3, 4, 5, 6, 7, 8, 9, 10, 15, 20, 25, 30, 35, 40, 45, 50, 55, 60, 65, 70, 75, 80, 85, 90, 95, 100 or more amino acids at its N-terminus and/or at its C-terminus and/or internally.

A "variant" as used herein, can alternatively or additionally be characterised by a certain degree of sequence identity to the parent polypeptide from which it is derived. More precisely, a variant in the context of the present invention exhibits at least 30% sequence identity, preferably at least 40% sequence identity, preferably at least 50% sequence identity, more preferably at least 60% sequence identity, more preferably at least 70% sequence identity, more preferably at least 80% sequence identity, even more preferably at least 90% sequence identity, and most preferably at least 95% sequence identity to its parent polypeptide. Preferably, the variants of the present invention exhibit the indicated sequence identity, and preferably the sequence identity is over a continuous stretch of 20, 30, 40, 45, 50, 60, 70, 80, 90, 100 or more amino acids. The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) *Proc. Natl. Acad. Sci. USA* 90: 5873-5877), with hmmalign (HMMER package, http://hmmer.wustl.edu/) or with the CLUSTAL algorithm (Thompson, J. D., Higgins, D. G. & Gibson, T. J. (1994) *Nucleic Acids Res.* 22, 4673-80) available e.g. on http://www.ebi.ac.uk/Tools/clustalw/ or on http://www.ebi.ac.uk/Tools/clustalw2/index.html or on http://npsa-pbil.ibcp.fr/cgi-bin/npsa_automat.pl?page=/NPSA/npsa_clustalw.html. Preferred parameters used are the default parameters as they are set on http://www.ebi.ac.uk/Tools/clustalw/ or http://www.ebi.ac.uk/Tools/clustalw2/index.html. The grade of sequence identity (sequence matching) may be calculated using e.g. BLAST, BLAT or BlastZ (or BlastX). Preferably, sequence matching analysis may be supplemented by established homology mapping techniques like Shuffle-LAGAN (Brudno M., Bioinformatics 2003b, 19 Suppl 1:I54-I62) or Markov random fields. When percentages of sequence identity are referred to in the present application, these percentages are calculated in relation to the full length of the longer sequence, if not specifically indicated otherwise.

"Non-conservative substitutions" or "non-conservative amino acid exchanges" are defined as exchanges of an amino acid by another amino acid listed in a different group of the six standard amino acid groups shown below:
(1) hydrophobic: Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

"Conservative substitutions" are defined as exchanges of an amino acid by another amino acid listed within the same group of the six standard amino acid groups shown above. As used herein, the term "derivative" of a polypeptide refers to a polypeptide that has been chemically modified so that it comprises other chemical groups than the 20 naturally occurring amino acids. The polypeptide from which the derivative derives is also known as the parent polypeptide. This parent polypeptide can be a naturally occurring protein but can also be a protein variant as defined above. Chemical modifications of a polypeptide may provide advantageous properties as compared to the parent polypeptide, e.g. enhanced stability, increased biological half-life, increased water solubility. Chemical modifications applicable to the derivatives usable in the present invention include without limitation: PEGylation, glycosylation of non-glycosylated parent polypeptides, or the modification of the glycosylation pattern present in the parent polypeptide.

A "biological activity" as used herein, refers to any activity a polypeptide may exhibit, including without limitation: enzymatic activity; binding activity to another compound (e.g. binding to another polypeptide, in particular binding to a receptor, binding to a nucleic acid); inhibitory activity (e.g. enzyme inhibitory activity); activating activity (e.g. enzyme-activating activity); or toxic effects. It is not required that the variant or derivative exhibits such an activity to the same extent as the parent polypeptide. A variant is regarded as a variant within the context of the present application, if it exhibits the relevant activity to a degree of at least 1% of the activity of the parent polypeptide. Likewise, a derivative is regarded as a derivative within the context of the present application, if it exhibits the relevant activity to a degree of at least 1% of the activity of the parent polypeptide.

Generally known and practiced methods in the fields of molecular biology, cell biology, protein chemistry and antibody techniques are fully described in the continuously updated publications "Molecular Cloning: A Laboratory Manual", (Sambrook et al., Cold Spring Harbor); Current Protocols in Molecular Biology (F. M. Ausubel et al. Eds., Wiley & Sons); Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al., Eds., Wiley & Sons). Known techniques relating to cell culture and media are described in "Large Scale Mammalian Cell Culture (Hu et al., Curr. Opin., Biotechnol. 8: 148, 1997); "Serum free Media" (K. Kitano, Biotechnol. 17:73, 1991); and "Suspension Culture of Mammalian Cells" (Birch et al. Bioprocess Technol. 19: 251, 1990).

Methods directed to stem cells are described in "Teratocarcinoma and embryonic stem cells: A practical approach" (E. J. Robertson, ed., Press Ltd, 1987); "Guide to Techniques in Mouse Development" (P. M. Wassermann et al. eds., Academic Press, 1993); "Embryonic Stem Cell Differentiation in Vitro" (M. V. Wiles, Meth. Enzymol. 225: 900, 1993); "Properties and uses of Embryonic Stem Cells: Prospects for Application to Human Biology and Gene Therapy" (P. D. Rathjen et al., 1993); "Embryonic Stem Cells, Methods and Protocols" (K. Turksen ed., Humana Press, 2002) and "Human Embryonic Stem Cells" (A. Chiu and M. S. Rao, Humana Press, 2003). An overview of stem cell differentiation is provided by Robertson, Meth. Cell Biol. 75: 173, 1997 and Pedersen, Reprod. Fertil. Dev. 10: 31, 1998.

Methods relating to biological engineering techniques are described in "Bioprozesstechnik" (H. Chmiel Hrsg., Gustav Fischer Verlag 1991); "Bioreaktoren und periphere Einrichtungen. Ein Leitfaden für die Hochschulausbildung, für Hersteller und Anwender" (Winfried Storhas, Springer Verlag 1994); "Bioprocess Engineering Principles" (Pauline M. Doran, Academic Press 1997) and "Bioprocess Engineering: Basic Concepts" (Michael L-Shuler, Prentice Hall 2000). Reagents, media and kits described herein can be obtained from any known commercial provider, such as Sigma, Bio-Rad, Stratagene, and Roche.

EMBODIMENTS OF THE INVENTION

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect the present invention provides a fusion protein comprising
a) a protein transduction domain (PTD) comprising 6 to 12 (e.g. 6, 7, 8, 9, 10, 11, or 12) basic amino acids;
b) at least one transcription factor.

In preferred embodiments, the PTD comprises 7 to 11, more preferably 8 to 10, even more preferably 9 basic amino acids. Preferably, the term "basic amino acids" includes the following amino acids: Asn, Gln, His, Lys, Arg. Particularly preferred basic amino acids are Lys and Arg.

A fusion protein according to the first aspect can also comprise a variant or a derivative of a naturally occurring transcription factor. The terms "variant" and "derivative" are defined above.

Within a preferred embodiment of the present invention, and particularly in a preferred embodiment of the first aspect, the PTD further comprises hydrophobic amino acids. It is thereby preferred that the amino acids are selected from the group consisting of valine, (iso)leucine, methionine, phenylalanine, cysteine, alanine, tyrosine, histidine, threonine, serine, proline, glycine, arginine and lysine, wherein valine, (iso)leucine, methionine, phenylalanine and cysteine are particularly preferred. Preferably, the PTD comprises between 1 and 12 (e.g. 1, 2, 3, 4, 5, 6, 7, 8, 9, 10, 11, or 12) of such hydrophobic amino acids, more preferably between 1 and 8 hydrophobic amino acids, even more preferably between 1 and 4 hydrophobic amino acids.

Within a further preferred embodiment of the present invention, and particularly in a preferred embodiment of the first aspect, the PTD consists of HIV TAT, a TAT peptide with protein transduction activity, Penetratin, HSV-VP22, Transportan, K-FGF, Oligoarginine or Arg-9 or peptides consisting of combinations of Arginine and Lysine residues.

In another preferred embodiment of the present invention, and particularly in a preferred embodiment of the first aspect, the PTD consists of at least 8 amino acids but not more than 10, 12, 13, 14, 15, 16, 17, 18, 19 or 20 amino acids, preferably between 8 to 18 amino acids, more preferably between 10 to 16 amino acids.

Within a preferred embodiment of the present invention, and particularly in a preferred embodiment of the first aspect, the transcription factor is selected from the group consisting of: stem cell factors, such as Oct4, Sox2, nanog, klf4, lin28, hTERT, myc, SV40; differentiation factors, such as hox-genes, pax genes; reprogramming factors, such as HMGB, Msx1; tumor suppressors, such as p53, Pten; and anti-apoptose factors, such as bcl-2; as well as any combination of the foregoing and variants and derivatives of any of the foregoing. Sox2 and Oct4, alone or in combination, are most preferred transcription factors of the present invention. The transcription factors to be used may also comprise factors which comprise one or more mutations of amino acids compared to their native counterparts, as long as they encompass the same or a nearly the same cellular activities. Thus, the transcription factor within the fusion protein of the invention may be a variant (as defined above) or a derivative (as defined above) of Sox2 or Oct4. For further information on transcription factors see http://en.wikipedia.org/wiki/Transcription_factor-cite_note-pmid8870495-2

Within the present invention, and particularly in a preferred embodiment of the first aspect, it is further preferred that the fusion protein comprises a nuclear localization signal (NLS). Within the present invention any NLS can be used which is known to a person skilled in the art as suitable for the purpose of the present invention. It is, however, preferred to select the NLS of the SV40 type, wherein it is most preferred to select the transcription factor thus to comprise a NLS such as Oct4. A particularly preferred NLS has the following sequence: KKKRKV (SEQ ID NO: 19).

Within the present invention, and particularly in a preferred embodiment of the first aspect, it is further preferred that the fusion protein comprises an artificial transactivating domain (ATAD) such as VP16. Said ATAD may replace the TAD present in the transcription factor part of the fusion proteins of the present invention and/or an ATAD may be present in addition to the TAD present in the transcription factor part.

VP16 is a domain derived from herpes simplex virus type 1 viral protein 16 that exhibits strong transactivation activity when fused to a DNA binding domain. An ATAD fused to the transcription factor is thought to enhance the transactivating activity of the internalized fusion protein. Any ATAD conferring transactivating activity might be used, either derived from biological origins or artificially composed.

Within the present invention, and particularly in a preferred embodiment of the first aspect, it is further preferred that the fusion protein comprises linkers between functional peptides.

Within the present invention any linker can be used which is known to a person skilled in the art as suitable for the purpose of the present invention. It is, however, preferred to select the linker from the group consisting of Proline, Glycine, Alanine, Leucine, Glutamic acid, Threonine, Serine. Proline, Alanine, Leucine and Glutamic acid are mostly preferred.

Within the present invention, and particularly in a preferred embodiment of the first aspect, it is further preferred that the fusion protein comprises at least one end group at the amino-terminus. Within the present invention any end group can be used which is known to a person skilled in the art as suitable for the purpose of the present invention. It is, however, preferred to select the end group from the group consisting of Glycine and Alanine, wherein Glycine is particularly preferred.

Within the present invention, it is further preferred that the fusion protein comprises, consists of, or essentially consists of an amino acid sequence as shown in SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8. It is particularly preferred that the fusion protein comprises, consists of, or essentially consists of an amino acid sequence as shown in SEQ ID NO: 2 and SEQ ID NO: 5.

| Fusion protein sequence | Composition of the fusion protein |
|---|---|
| SEQ ID NO: 1 | Oct4NTH |
| SEQ ID NO: 2 | Oct4TH |
| SEQ ID NO: 3 | HTNOct4 |
| SEQ ID NO: 4 | HTOct4 |
| SEQ ID NO: 5 | Sox2NTH |
| SEQ ID NO: 6 | Sox2TH |
| SEQ ID NO: 7 | HTNSox2 |
| SEQ ID NO: 8 | HTSox2 |

"Oct4" and "Sox2" refer to the transcription factors as defined above.

"N" refers to the presence of the nuclear localisation signal sequence KKKRKV (SEQ ID NO: 19), which is encoded by the nucleotide sequence 5'-AAG AAG AAG AGG AAG GTG-3' (SEQ ID NO: 20) as shown in FIG. 1B.

"T" refers to the basic TAT peptide GRKKRRQRRRPP (SEQ ID NO: 21), which is encoded by the nucleotide sequence 5'-GGT CGC AAG AAA CGT CGC CAA CGT CGC CGT CCG CCT-3' (SEQ ID NO: 22) as shown in FIG. 1B. This basic peptide GRKKRRQRRRPP is part of the HIV-1 TAT protein, more precisely this basic peptide constitutes amino acids 48-59 of the HIV-1 TAT protein.

The letter "H" denotes the presence of a His-Tag. C-terminally tagged proteins (SEQ ID NO: 1, 2, 5, and 6) comprise a His-Tag consisting of 8 His residues, while N-terminally tagged proteins (SEQ ID NO: 3, 4, 7, and 8) comprise a His-Tag consisting of 6 His residues (see FIG. 1B).

In a second aspect the present invention provides a fusion protein comprising: a) at least one transcription factor, wherein from 6 to 12 amino acids (e.g. 6, 7, 8, 9, 10, 11, or 12) of said transcription factor have been replaced by basic amino acids, preferably by surface mutagenesis.

Preferably, the term "basic amino acids" includes the following amino acids: Asn, Gln, His, Lys, Arg. Particularly preferred basic amino acids are Lys and Arg. The term "non-basic amino acids" refers to all amino acids naturally occurring in proteins except Asn, Gln, His, Lys, Arg.

The purpose of this replacement of amino acids is that said 6 to 12 basic amino acids can function as a PTD. Preferably, amino acids located at the surface of the transcription factor are replaced by basic amino acids. Preferably, the replaced amino acids are non-basic amino acids. However, it is also possible within the second aspect of the invention to replace one or more basic amino acid selected from Asn, Gln or His by the particularly preferred basic amino acids Lys and Arg.

The fusion protein according to the second aspect has the advantage that no additional PTD needs to be added to the transcription factor. Without wishing to be bound by a particular theory, the inventors believe that fusion proteins according to the second aspect may have enhanced solubility and/or stability properties.

Within the present invention, embodiments are also included which constitute a combination of the fusion proteins of the first aspect and the fusion proteins of the second aspect. In particular, a fusion protein of the invention may (i) comprise a PTD comprising basic amino acids and (ii) may further comprise basic amino acids that were introduced into the sequence of the transcription factor by replacing non-basic amino acids. A fusion protein according to this combination of the first and the second aspect may have 6 to 12 basic amino acids that may be divided between the PTD and the sequence of the transcription factor. For example, 3 non-basic amino acids in the transcription factor can be replaced by basic amino acids and the fusion protein additionally comprises a PTD comprising only 3 to 9 basic amino acids. In these fusion proteins constituting a combination of the first and the second aspect, the length of the PTD may be significantly shortened due to the presence of basic amino acids within the transcription factor.

Within a preferred embodiment of the second aspect, the transcription factor is selected from the group consisting of: stem cell factors, such as Oct4, Sox2, nanog, klf4, 1 in28, hTERT, myc, SV40; differentiation factors, such as hox-genes, pax genes; reprogramming factors, such as HMGB, Msx 1; tumor suppressors, such as p53, Pten; and anti-apoptose factors, such as bcl-2; as well as any combination of the foregoing. Sox2 and Oct4, alone or in combination, are most preferred transcription factors of the present invention. The transcription factors to be used may also comprise factors which comprise one or more mutations of amino acids compared to their native counterparts, as long as they encompass the same or a nearly the same cellular activities.

Within a preferred embodiment of the second aspect, it is further preferred that the fusion protein comprises a nuclear localization signal (NLS).

Within the present invention any NLS can be used which is known to a person skilled in the art as suitable for the purpose of the present invention. It is, however, preferred to select the NLS of the SV40 type, wherein it is most preferred to select the transcription factor to be modified to comprise a NLS such as Oct4.

Within a preferred embodiment of the second aspect, it is further preferred that the fusion protein comprises an artificial transactivating domain (ATAD) such as VP16. Said ATAD may replace the TAD present in the transcription factor part of the fusion proteins of the present invention and/or an ATAD may be present in addition to the TAD present in the transcription factor part. An ATAD fused to the transcription factor is thought to enhance the transactivating activity of the internalized fusion protein. Any ATAD conferring transactivating activity might be used, either derived from biological origins or artificially composed.

Within a preferred embodiment of the second aspect, the fusion protein comprises linkers between functional peptides. Any linker can be used which is known to a person skilled in the art as suitable for the purpose of the present invention. It is, however, preferred to select the linker from the group consisting of Proline, Glycine, Alanine, Leucine, Glutamic acid, Threonine, Serine. Proline, Alanine, Leucine and Glutamic acid are mostly preferred.

Within a preferred embodiment of the second aspect, it is further preferred that the fusion protein comprises at least one end group at the amino-terminus. Any end group can be used which is known to a person skilled in the art as suitable for the purpose of the present invention. It is, however, preferred to select the end group from the group consisting of Glycine and Alanine, wherein Glycine is particularly preferred.

In a third aspect, the present invention provides the use of the fusion protein according to the invention for the generation of induced pluripotent cells or for the differentiation of pluripotent cells.

It is thereby possible to use the fusion protein of the present invention for the generation or differentiation of any kind of pluripotent cells, it is, however, preferred to use the fusion protein of the invention for the generation or differentiation of pluripotent stem cells.

Pluripotent stem cells have the ability to develop into all different types of cells found in the human body. Examples of pluripotent stem cells include embryonic stem cells derived from the inner cell mass of the embryonic blastocyst. Induced pluripotent stem cells are cells derived from adult or differentiated cells.

To use the fusion protein(s) of the present invention for the generation of induced pluripotent cells, the protein(s) is (are) preferably applied to adult and differentiated cells in form of a composition.

The present invention therefore further provides in a fourth aspect a composition containing at least one fusion protein of the present invention and a stabilizer or mixtures of stabilizers, wherein the stabilizer is preferably a lipid rich serum, e.g. Albumax.

A "stabilizer" usable within the present invention and in particular usable in accordance with the fourth aspect comprises chemicals, peptides, proteins or compounds that are able to enhance the cellular uptake of proteins. Such "stabilizers" include compounds that i) are able to enhance stability or solubility of the fusion proteins such as serum replacement (SR) or chemical chaperones; ii) are able to enhance penetration of the cell membrane such as hydrophobic counterions like pyrene-butyrate, streptolysine-A, protein transfection reagents; iii) are able to enhance endosomal release of translocated proteins such as chloroquine, sucrose, fusogenic peptides.

Target cells are all type of cells known to a person skilled in the art as suitable for the inventive purpose and are preferably selected from the group consisting of adult stem cells, somatic cells of mammals, respectively, such as cells of flies (e.g. *D. melanogaster*, worms (e.g. *C. elegans*) as well as lower eukaryotes (e.g. yeast, e.g. *S. cerevisiae*). Mostly preferred are human adult stem cells such as hematopoetic stem cells or mesenchymal stem cells or neural stem cells or chord blood cells or dental pulp derived stem cells or skin stem cells.

In a fifth aspect, the present invention further provides a method for generating the fusion protein of the invention. This method comprises the steps:

a) constructing a DNA sequence comprising a sequence encoding for a PTD and a sequence encoding for a transduction factor;
b) cloning the DNA sequence into a suitable vector;
c) transforming the vector in a suitable expression system;
d) optionally purifying the expressed fusion proteins.

Culture media for transduction experiments comprise a glycerol stock solution (with a concentration of from 0.1 µM to 10 µM, preferably 3 µM for Sox2NTH and 1.5 µM for Oct4TH) of the proteins 1:20 or 1:50 with Advanced D-MEM (Dulbecco's modified Eagle) medium (Invitrogen) supplemented with of from 0.1% to 10%, preferably 5%, FCS (fetal calf serum); of from 0.1% to 5%, preferably 0.5% Albumax II; of from 0.1% to 5%, preferably 0.5% IST; of from 0.1% to 5%, preferably 0.5% Sodium Pyruvat; of from 0.1% to 5%, preferably 0.5%, non-essential amino acids; of from 0.1% to 5%, preferably 1% glutamine; and of from 10 µM to 500 µM, preferably 100 µM, b-mercaptoethanol.

Within this method, the vector is preferably selected from the group consisting of IPTG-inducible expression vectors, wherein a plasmid vector, such as a vector based on pTriEx expression plasmid, is particularly preferred. The present invention preferably includes flexible expression vectors that allow rapid cloning of derivatives carrying peptide tags either at the amino-terminus or carboxy-terminus of the fusion protein.

The expression of the protein can be carried out in any expression system known to a person skilled in the art as suitable for the inventive purpose, such as eucaryotic expression systems such as yeasts (*S. cerevisiae* or *P. pastoris*), bacterial expression systems, insect cells (sf9) or mammalian expression systems such as CHO, 293 or HEK cells. Moreover, the fusion proteins might be derived from a cell-free expression system such as bacterial or rabbit reticulocyte lysates. In one embodiment, it is preferred to transform the vector in an *E. coli* expression system, wherein *E. coli* BL21 (DE3) is particularly preferred. In another embodiment, it is preferred to employ the vector in a cell-free expression system, such as bacterial or rabbit reticulocyte lysates. It is further preferred in this latter embodiment to omit the optional purifying step d). The cell-free expression system containing the fusion protein of the invention can subsequently be used—without isolating the fusion protein from the cell-free expression system—to generate induced pluripotent cells by contacting said cell-free expression system with a suitable target cell.

In a sixth aspect, the present invention provides a nucleotide sequence encoding the fusion protein according to the present invention, in particular a nucleotide sequence encoding the fusion protein according to first and the second aspect of the present invention.

In a seventh aspect, the present invention provides a method for generating induced pluripotent cells, comprising the step:
 a) contacting at least one fusion protein according to the first aspect, the second aspect, or the combination of the first and the second aspect with at least one target cell.

In an eighth aspect, the present invention provides a method for generating induced pluripotent cells, comprising the step:
 a) carrying out steps a) to c) of the method according to the fifth aspect, wherein step c) is carried out in a cell-free expression system; and
 b) contacting the cell-free expression system of step a) with at least one target cell.

It is possible in the methods of the seventh and the eighth aspect, that the fusion protein(s) are of the same amino acid sequence or possess different amino acid sequences. The present invention thereby relates in particular to methods, wherein the fusion protein(s) possess one or more different transcription factors.

Within these methods according to the seventh and the eight aspects, the time for contacting the fusion protein(s) with the target cell(s) can be any time known to a person skilled in the art as suitable for the inventive purpose, but is preferably from 1 minute to several days, preferred from 30 minutes to 60 days, even more preferred from 6 hours to 60 days, more preferred from 6 hours to 21 days, even more preferred from 16 hours to 12 days and most preferred from 4 days to 12 days. It is thereby possible to contact fusion proteins of different amino acid sequences separately or simultaneously and for the same or different time periods.

Within these methods according to the seventh and the eight aspects, the fusion protein(s) of the invention can be applied in the same or different concentrations and/or doses. It is thereby possible to apply the fusion protein(s) in any concentration(s) and dose(s) known to a person skilled in the art as suitable for the inventive purpose, however, it is preferred to apply the fusion protein(s) in concentrations up to 1 micro-M, preferred from 10 nM to 500 nM and most preferred from 25 nM to 300 nM.

The contacting of the fusion protein(s) and the target cell(s) can be carried out by any method known to a person skilled in the art as suitable for the inventive purpose, such as the insertion of the fusion protein(s) of the present invention by use of carbon nano-particles, preferably single-walled carbon nanotubes. Preferred methods in this context are non-covalent linkage and adhesion. It is thereby possible to contact different fusion proteins according to the same or different methods.

Within these methods according to the seventh and the eight aspects, all type of cells known to a person skilled in the art as suitable for the inventive purpose can be used as target cells. Preferably, target cells are selected from the group consisting of adult stem cells, somatic cells of mammals, respectively, such as cells of flies (e.g. *D. melanogaster*, worms (e.g. *C. elegans*) as well as lower eukaryotes (e.g. yeast, e.g. *S. cerevisiae*). Mostly preferred are human adult stem cells such as hematopoetic stem cells or mesenchymal stem cells or neural stem cells or chord blood cells or dental pulp derived stem cells or skin stem cells.

Within the present invention, it is further preferred that the amino acids conferring translocation activity are included into the native sequence not by fusion to a translocating peptide but limited mutation of amino acids that are exposed to the solvent. For instance the translocating activity of basic residues such as Arginine or Lysine might be employed by substituting various amino acids to Arginine thereby increasing the local and/or overall basicity of the protein. This kind of supercharging might involve one part of the protein or the whole surface.

Regarding the above defined methods for generating induced pluripotent cells, the present invention is particularly useful to apply different proteins with different defined concentrations and different defined incubation times. It is thereby possible to optimize the reprogramming process by e.g. initially enhancing the proliferative potential of target cells by one or more factors and then induce pluripotency by the application of other factor(s). The method comprising the following steps is particularly preferred: Incubating target cells with factors enhancing the proliferation such as myc or hTERT for up to two weeks, preferably 1 week. In a second step cells will be incubated with Oct4 and Sox2 to induce pluripotency up to two weeks, preferably 1 week. The intracellular delivery of each factor will be preferably carried out by viral transduction, more preferably by nano-particle-assisted proteins delivery and most preferably by protein transduction using fusion proteins described above or combinations thereof.

Within the present invention, it is further preferred that the reprogramming media contains chemicals, peptides, proteins or compounds that are able to enhance the cellular uptake of proteins. These include compounds that i) are able to enhance stability or solubility of the fusion proteins such as serum replacement (SR) or chemical chaperones; ii) are able to enhance penetration of the cell membrane such as hydrophobic counterions like pyrene-butyrate, streptolysine-A, protein transfection reagents; iii) are able to enhance endosomal release of translocated proteins such as chloroquine, sucrose, fusogenic peptides. It is further preferred that endosomal release is enhanced by photoactivation of fluororophores that are either co-transduced or linked to the fusion protein.

Within the present invention, it is further preferred that the reprogramming media is composed of one or more cell-permeant proteins together with small molecules that are able to enhance the reprogramming activity and/or substitute reprogramming factors.

The invention is further described by the following figures:

FIG. 1A: Schematic presentation of N- and C-terminal tagged versions of the vector.

This vector contains all functional peptides for the recombinant production of cell-permeant proteins. Tags are: histidine tag (His), protein transduction domain (TAT) and nuclear localization signal (NLS). After cloning the gene of interest into one version of the vector it can be readily transferred to the other one by the same restriction sites.

FIG. 1B: Excerpt of the coding region of the vector.

Every DNA sequence encoding for a functional peptide module can be removed by a single-enzyme restriction hydrolysis. His tag encoding sequence is framed, TAT-coding sequence is given in bold, NLS is highlighted in grey and restriction sites are given in italics.

Figure 1C:
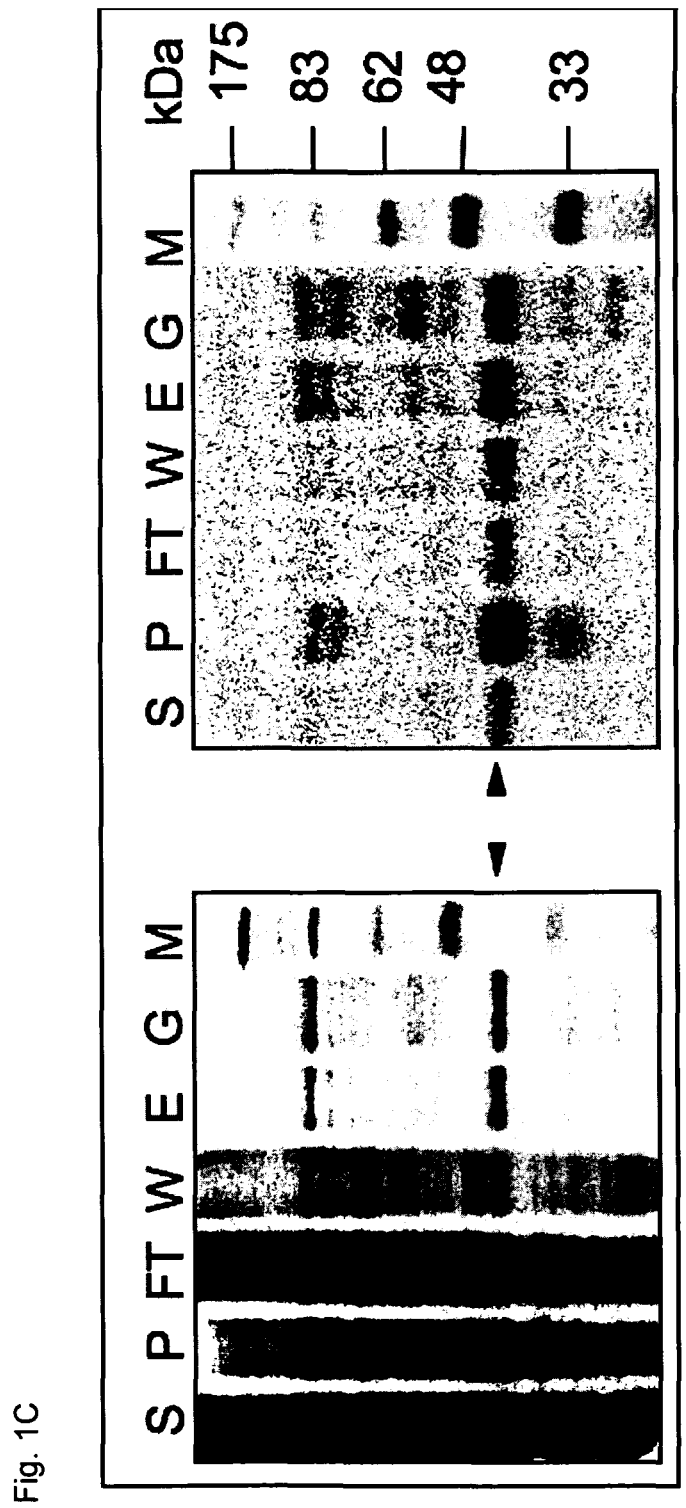

FIG. 1C: Ni-(II)-affinity chromatography purification of transducible proteins:

SDS/PAGE and western blot analysis of Sox2NTH

A specific antibody against Sox2 was used. S, supernatant of bacterial lysat; P, pellet; FT, flow through; W, wash fraction; E, eluted fraction; G, glycerol stock; M, marker.

Figure 1D:
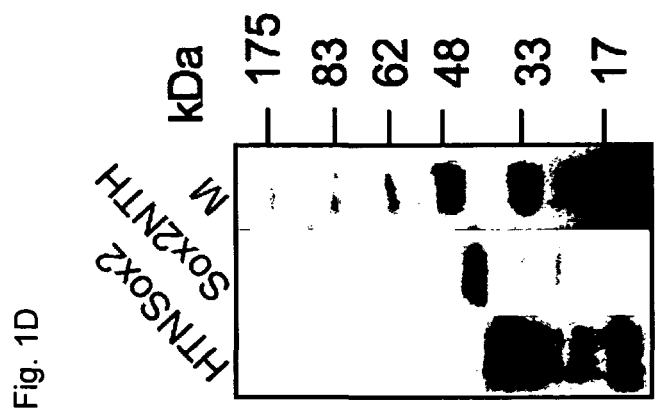

FIG. 1D: Western blot analysis employing a anti-His antibody comparing the eluat fractions of HTNSox2 and Sox2NTH.

Protein stocks were diluted 1:20 in cell culture medium.

Figure 1E:
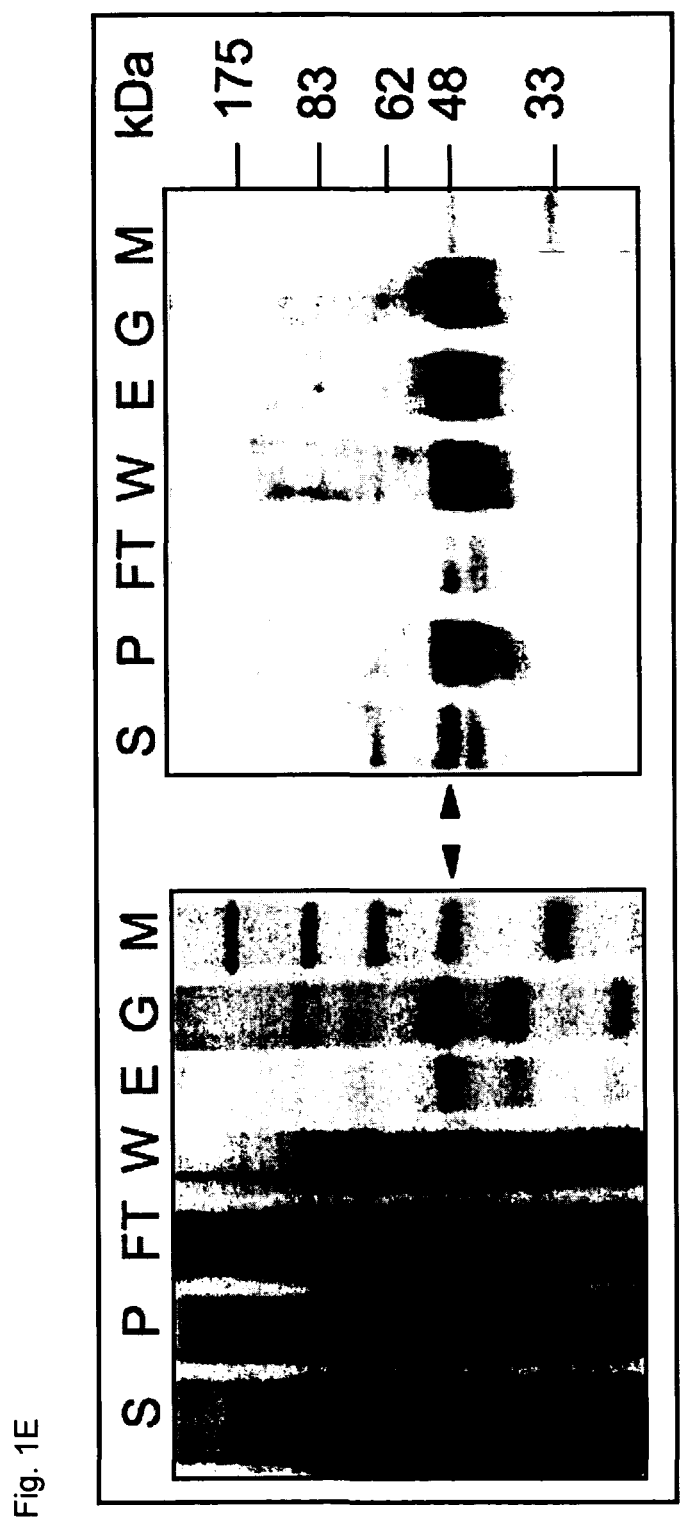

FIG. 1E: Ni-(II)-affinity chromatography purification of transducible proteins:

SDS/PAGE and western blot analysis of Oct4TH.

A specific antibody against Oct4 was used. S, supernatant of bacterial lysat; P, pellet; FT, flow through; W, wash fraction; E, eluted fraction; G, glycerol stock; M, marker.

Figure 1F:
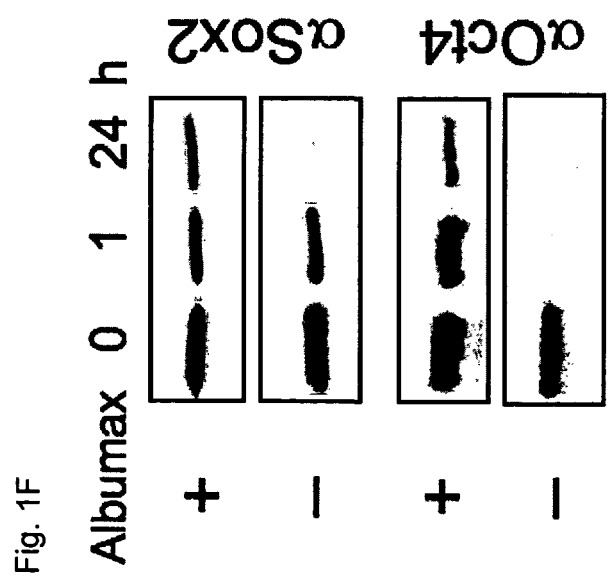

FIG. 1F: Western blot analysis showing the stabilization of Sox2NTH and Oct4TH under cell culture conditions after addition of 0.5% Albumax to the medium.

Protein stocks were diluted 1:20 in cell culture medium.

Figure 2:
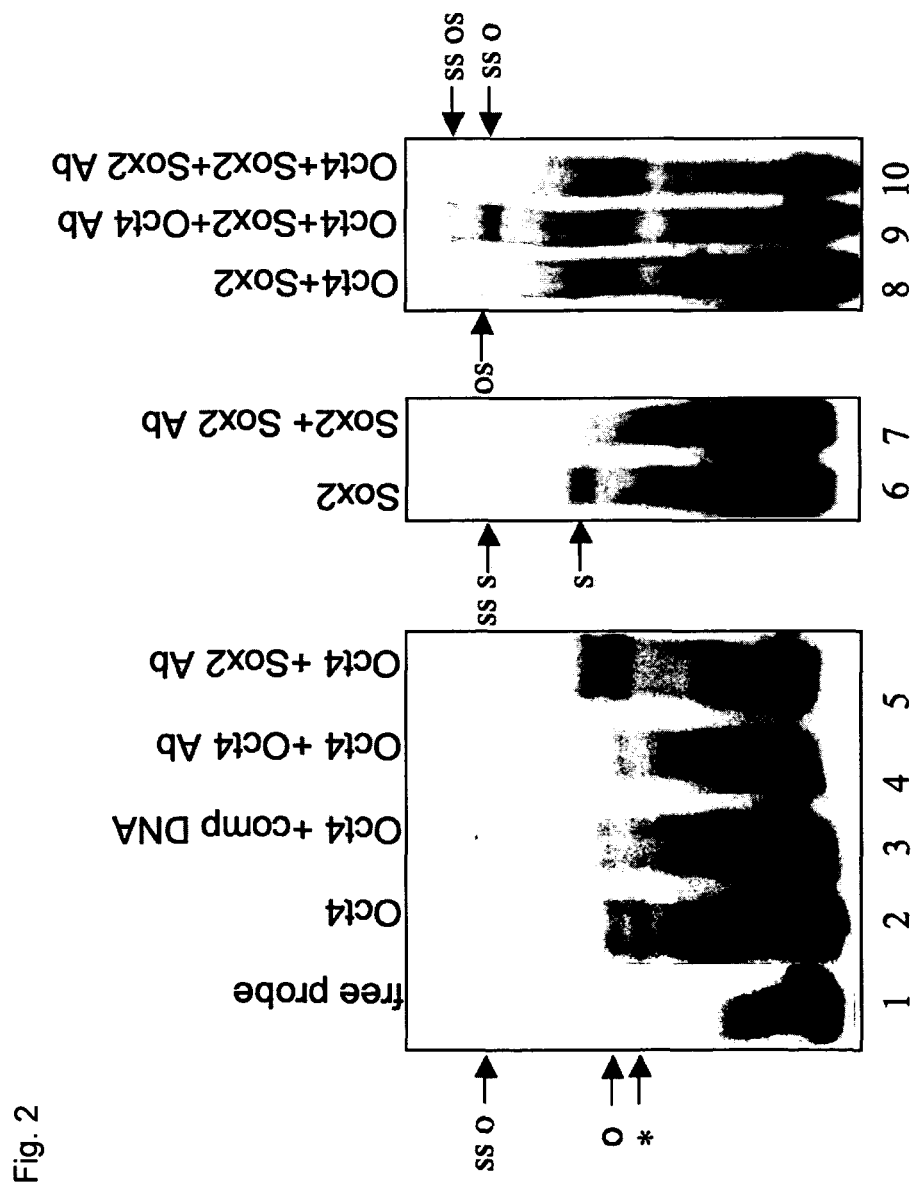

FIG. 2: DNA-binding ability of recombinant proteins in vitro.

EMSA shows binding of recombinant Oct4 ('o' marks shifted band of Oct4-DNA complex) and Sox2 (s) to a target DNA sequence from Nanog Promoter (lanes 2,6). To show the specificity of DNA binding, a 500-fold excess of the unlabeled probe was added (lane 3). The protein-DNA complexes were identified by a super shift (ss) through the respective specific antibodies (lanes 4, 5,7). When adding both proteins together to the probe a ternary complex was formed (os), whereas Oct4-DNA complex still represented the dominant band (lane 8). Both, Oct4-DNA binary complex as well as Oct4-Sox2-DNA ternary complex, were super-shifted employing Oct4 antibody (lane 9) whereas there was no super-shift observed employing Sox2 antibody (lane 10). Asterisk marks unspecific bands. Protein concentrations were 85 nM Oct4TH and 100 nM for Sox2NTH.

Figure 3A:
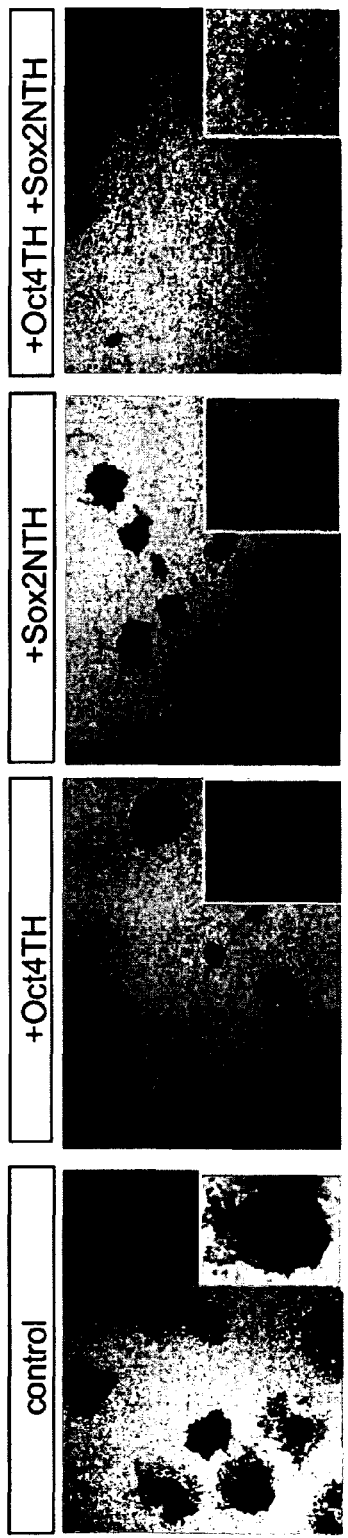

FIG. 3A: Alkaline phosphatase staining of Oct4-GiP ES cells treated with transducible Oct4 and Sox2 fusion proteins.

After adding Oct4TH and Sox2NTH to cell culture medium of mES cells for 5 days, colonies showed a more compact morphology than control cells and a stronger alkaline phosphatase (AP) staining (50-fold magnification).

Figure 3B:
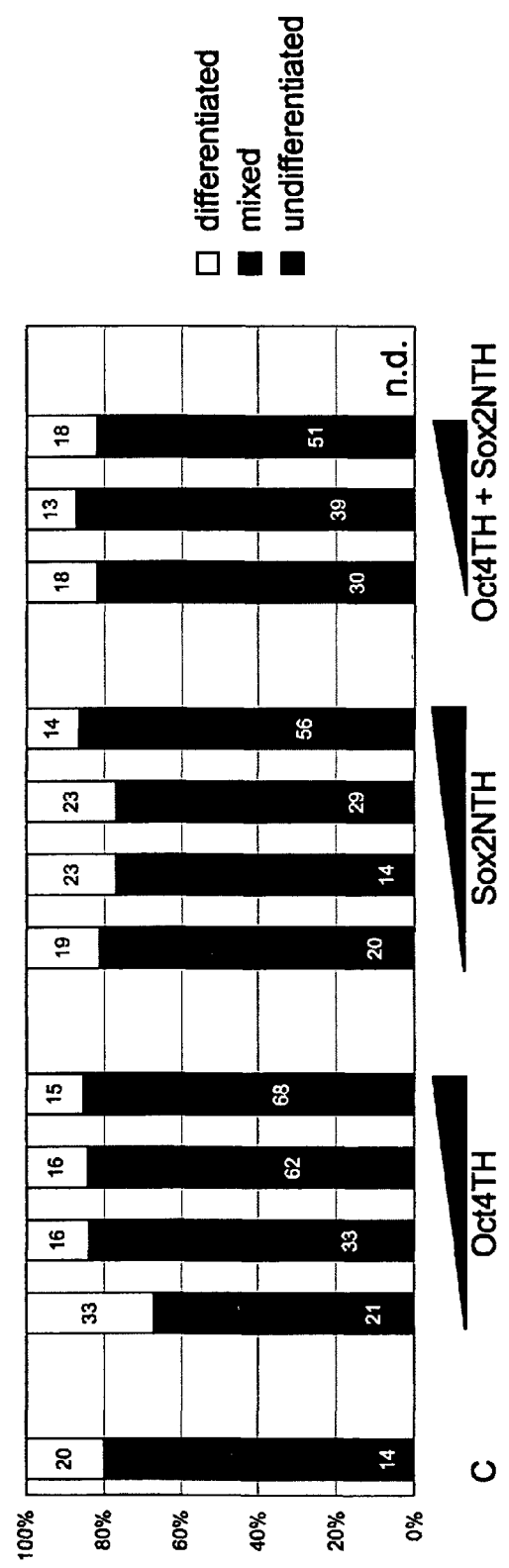

FIG. 3B: Alkaline phosphatase staining of Oct4-GiP ES cells treated with transducible Oct4 and Sox2 fusion proteins.

Quantification of colonies resulting from increasing concentrations of transducible proteins based on colony morphology and AP staining. Protein concentrations were 12.5, 25, 50 and 100 μM for Oct4TH and 20, 40, 75 and 150 μM for Sox2NTH. The effect of the combination of maximal protein concentrations was experimentally inaccessible due to the deleterious effect of glycerol of the stock solution at these high concentrations.

Figure 3C:
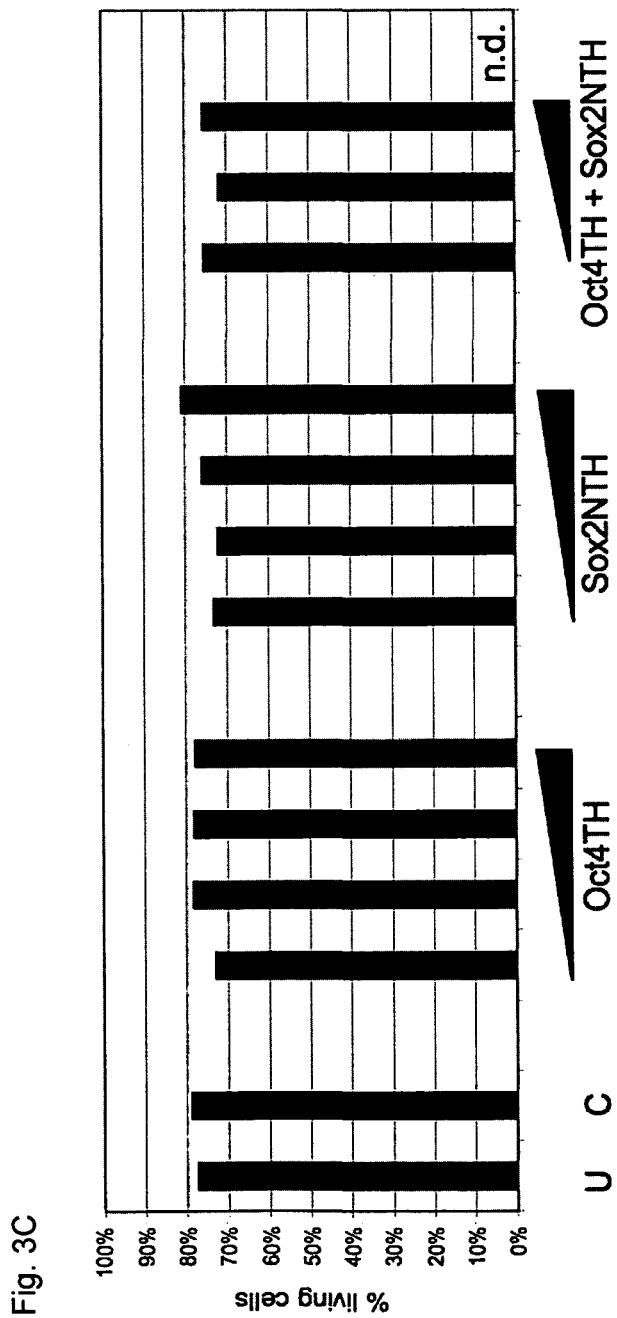

FIG. 3C: Alkaline phosphatase staining of Oct4-GiP ES cells treated with transducible Oct4 and Sox2 fusion proteins.

Flow cytometry analysis of cells kept under the same conditions as in B stained with Hoechst. Diagram shows the percentage of Hoechst negative cells.

Figure 4A:
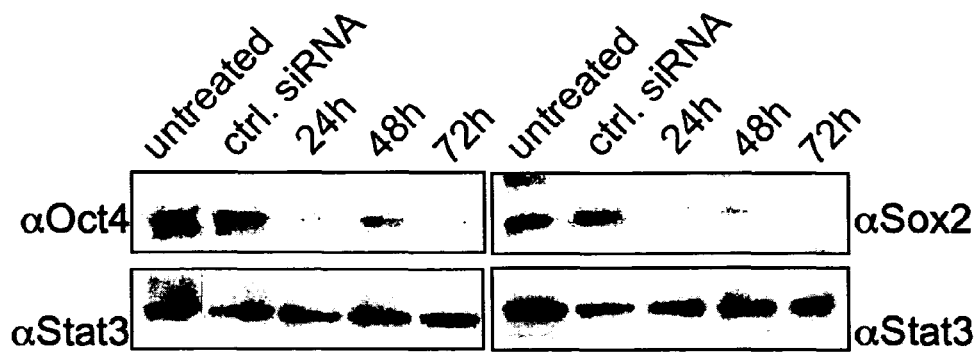

FIG. 4A: siRNA-mediated knock down of Pou5f1 and Sox2 in ES cells.

Western blot analysis demonstrates the down-regulation of target gene products after siRNA transfection in comparison to untreated cells or cells transfected with negative control siRNA. STAT3 was used as a loading control. Specific antibodies against Oct4, Sox2 and STAT3 were employed. Indicated time points are respective to the begin of siRNA transfection.

Figure 4B:
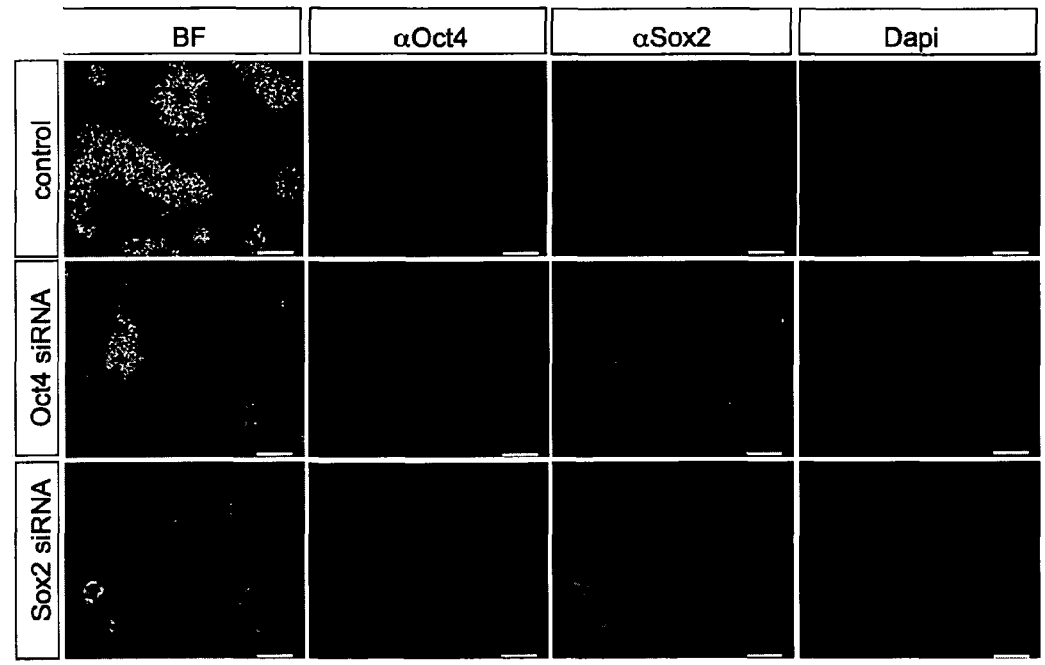

FIG. 4B: siRNA-mediated knock down of Pou5f1 and Sox2 in ES cells.

Immunofluorescence images of siRNA-treated ES cells 48 h after begin of siRNA transfection. Cell nuclei were stained using 4,6-di-amino-2-phenylindol (Dapi); BF, bright field. Scale bar=50 μM.

Figure 4C:
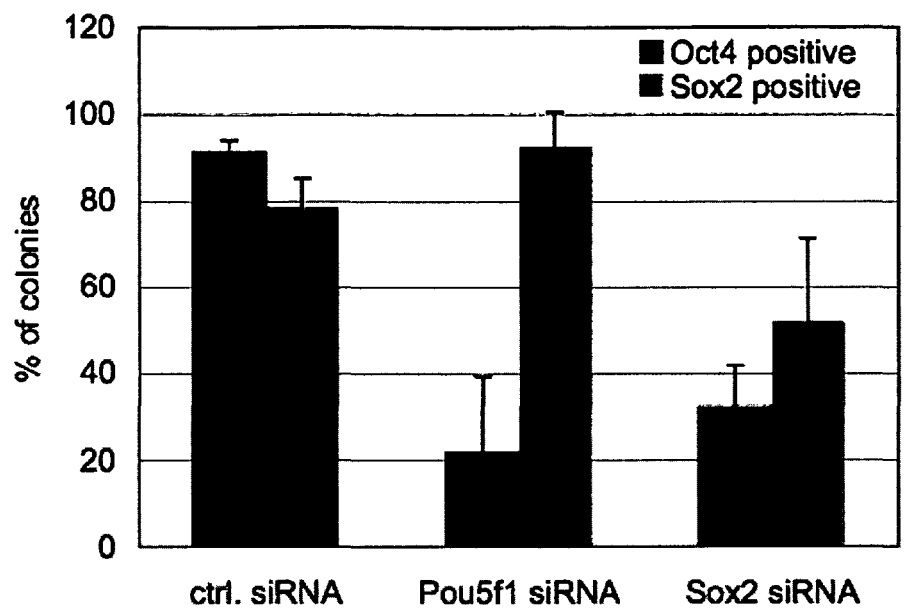

FIG. 4C: siRNA-mediated knock down of Pou5f1 and Sox2 in ES cells.

Quantification of Oct4- and Sox2-positive cells after siRNA k.d. of Pou5f1 or Sox2 and negative control siRNA. Error bars represent s.d.

Figure 4D:
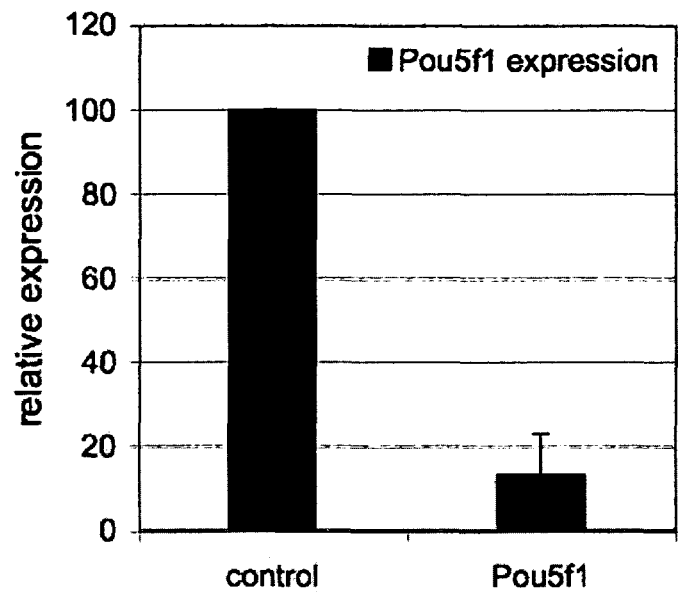

FIG. 4D: siRNA-mediated knock down of Pou5f1 in ES cells.

Real time RT-PCR analysis of relative expression levels of Pou5f1, 48 h after siRNA treatment in comparison to cells treated with negative control siRNA.

Figure 4E:
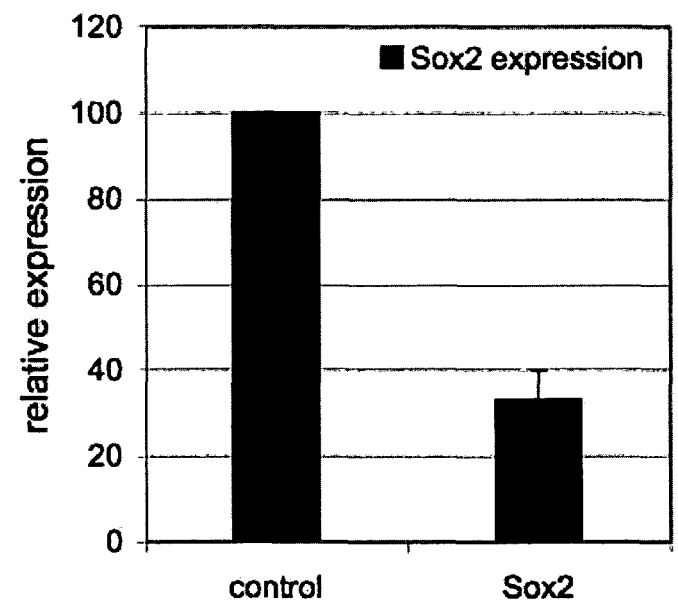

FIG. 4E: siRNA-mediated knock down of Sox2 in ES cells.

Real time RT-PCR analysis of relative expression levels of Sox2, 48 h after siRNA treatment in comparison to cells treated with negative control siRNA.

Figure 5A:
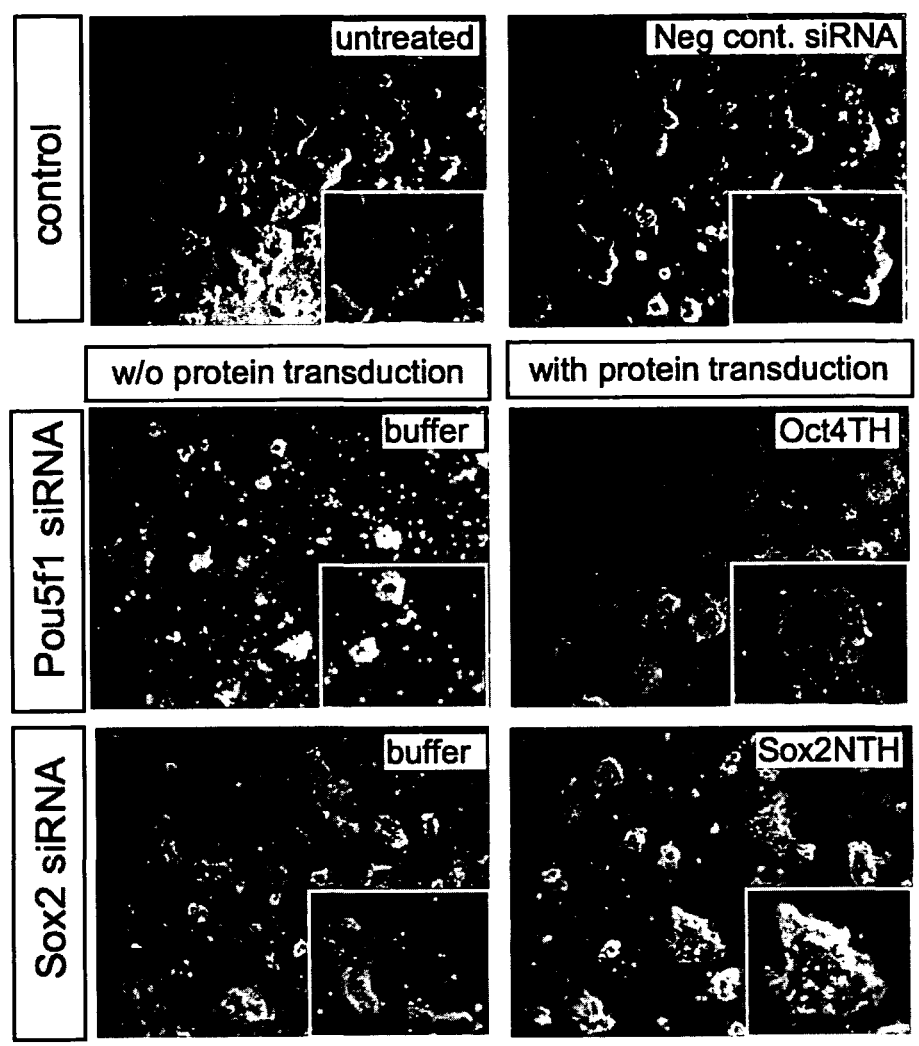

FIG. 5A: Compensation of siRNA knockdown of Pou5f1 and Sox2 by transduction of Oct4TH and Sox2NTH.

Mouse ES cells treated with siRNA against Pou5f1 or Sox2. Images of cells of the right panel are additionally treated with Oct4TH or Sox2NTH for 24 h. Images were taken 48 h after siRNA transfection, 50-fold magnification.

Figure 5B:
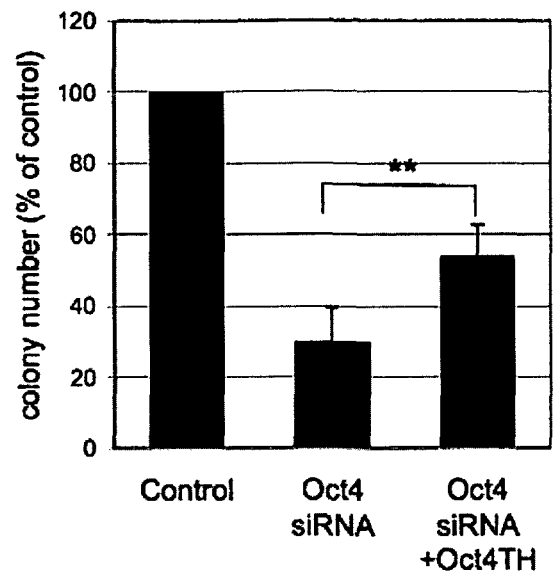

FIG. 5B: Compensation of siRNA knockdown of Pou5f1 and Sox2 by transduction of Oct4TH Quantification of colony numbers 48 h after siRNA transfection and 24 h after begin of protein treatment. Results are the mean of three independent experiments, error bars represent s.d., ** indicates P value<0.0001, * P<0.05, for undifferentiated colonies.

Figure 5C:
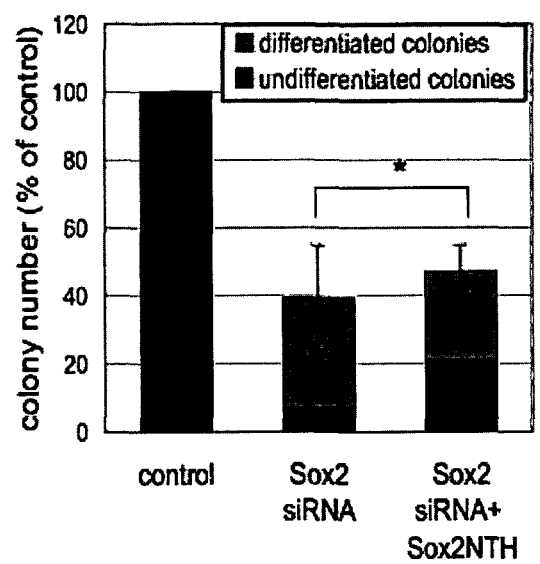

FIG. 5C: Compensation of siRNA knock down of Pou5f1 and Sox2 by transduction of Sox2NTH Quantification of colony numbers 48 h after siRNA transfection and 24 h after begin of protein treatment. Results are the mean of three independent experiments, error bars represent s.d., ** indicates P value<0.0001, * P<0.05, for undifferentiated colonies.

Figure 5D:
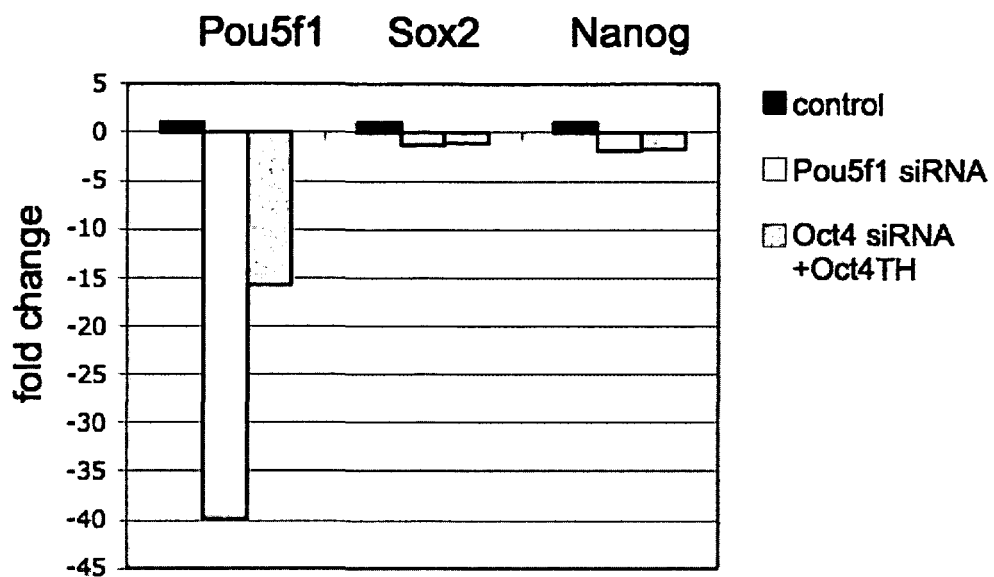

FIG. 5D: Compensation of siRNA knockdown of Pou5f1 and Sox2 by transduction of Oct4TH 48 h after siRNA transfection total RNA was collected and expression levels of Pou5f1, Sox2 and Nanog were analyzed by qRT-PCR. Results were normalized against the amount of b-Actin mRNA and are presented as the fold change in expression relative to treatment with negative control siRNA. Data presented are representative results for two independent experiments, analyzed in triplicate. Protein concentration was 100 nM Oct4TH.

Figure 5E:
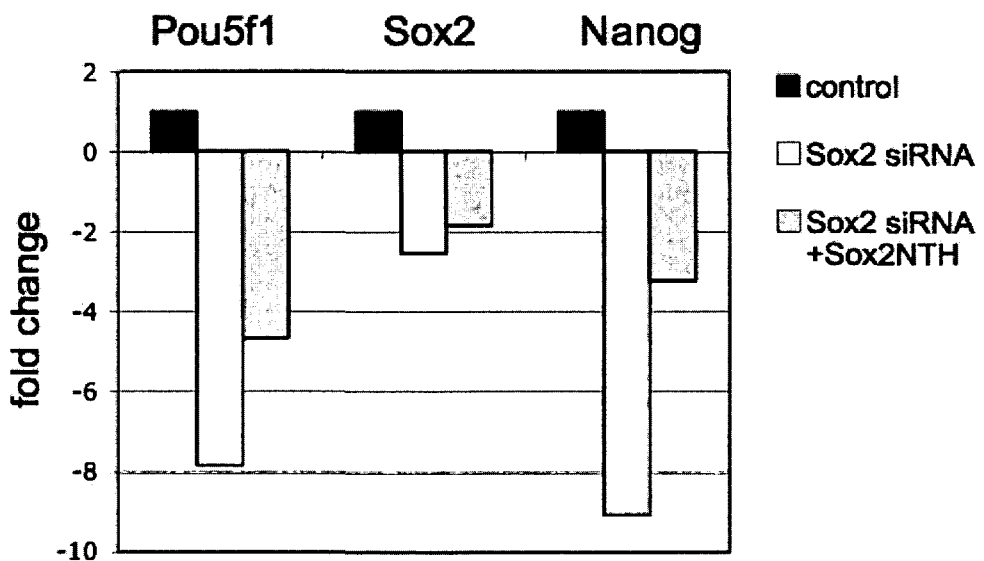

FIG. 5E: Compensation of siRNA knockdown of Pou5f1 and Sox2 by transduction of Sox2NTH 48 h after siRNA transfection total RNA was collected and expression levels of Pou5f1, Sox2 and Nanog were analyzed by qRT-PCR. Results were normalized against the amount of b-Actin mRNA and are presented as the fold change in expression relative to treatment with negative control siRNA. Data presented are representative results for two independent experiments, analyzed in triplicate. Protein concentration was 200 nM Sox2NTH.

FIG. 6A: Efficacy of iPS derivation depends on media composition.

For protein-induced iPS derivation optimized media conditions had to be explored, allowing highly efficient formation of iPS colonies and enhanced protein stability and solubility. Four different media were tested employing viral induction (Oct4, Sox2, Klf4, cMyc) of iPS cells. Oct4-GFP transgenic mouse embryonic fibroblasts (MEFs) were used. 24 hours after infection of 130 000 MEFs, the medium was changed to DMEM- or Knock-out-based ES cell medium, supplemented with Insulin-Transferrin-selenite and 5% fetal calf serum. After 5 days cells were splitted onto 10 cm dishes with irradiated MEF-feeder cells. Concurrently, the supplementation of the DMEM- or Knock-out-based ES media was changed to 15% serum replacement or remained with 15% FCS. 18 days after infection the number of colonies per 6 cm² was determined. FCS, fetal calf serum, KO, Knock-out medium, SRP, serum replacement.

FIG. 6B: KO and SRP increase percentage of Oct4-positive colonies.

Four different media were tested for viral induction of iPS cells. 24 hours after infection of 130 000 Oct4-GFP MEFs, the medium was changed to DMEM- or Knock-out-based ES cell medium, supplemented with Insulin-Transferrin-selenite and 5% FCS. After 5 days cells were splitted onto 10 cm dishes with irradiated MEF-feeder cells. Concurrently the supplementation of the DMEM- or Knock-out-based ES media was changed to 15% serum replacement or remained with 15% FCS. 18 days after infection the percentage of GFP positive colonies was determined.

FIG. 6C: Optimization of media composition to enhance solubility and stability of the fusion protein in different cell culture media.

Different media were tested for their ability to support protein transduction employing the Cre recombinase transduction system. HTNCre protein was added to culture media of CVI-5B Cre reporter cells (Peitz eta al., 2002) as indicated. 16 hours after transduction cells were fixed and stained for b-galactosidase activity. Recombinase efficiency was determined as the percentage of blue cells.

FIG. 6D: KO media containing 15% SRP supports formation of iPS colonies.

After viral transduction of reprogramming factors Oct4-GFP MEFs were cultured in KO media containing 15% SRP. Picture shows a colony 11 days after transduction. Inset shows fluorescence in the GFP channel confirming Oct4 transcriptional activity.

Figure 7A:
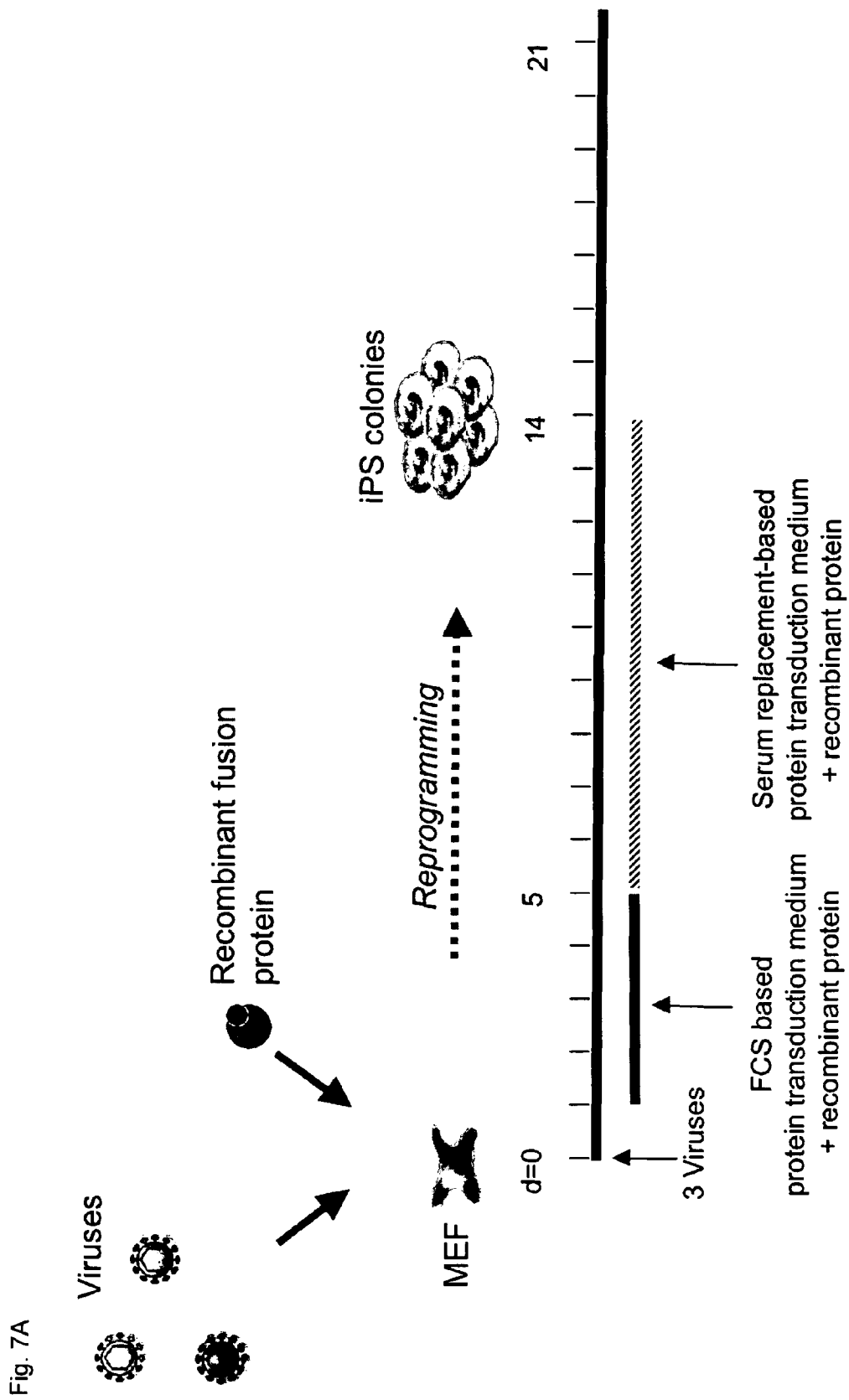

FIG. 7A: Schematic representation of an experiment aimed at identifying optimal concentrations of cell-permeant transcription factors to substitute factor-encoded viruses by recombinant fusion protein.

MEFs are plated and 1 day later transduced by three viruses. The lacking fourth factor is provided from day 1 on daily as a recombinant cell-permeant protein. At day 5 media is changed to SRP-based transduction media enhancing formation of Oct4-positive iPS colonies.

Figure 7B:
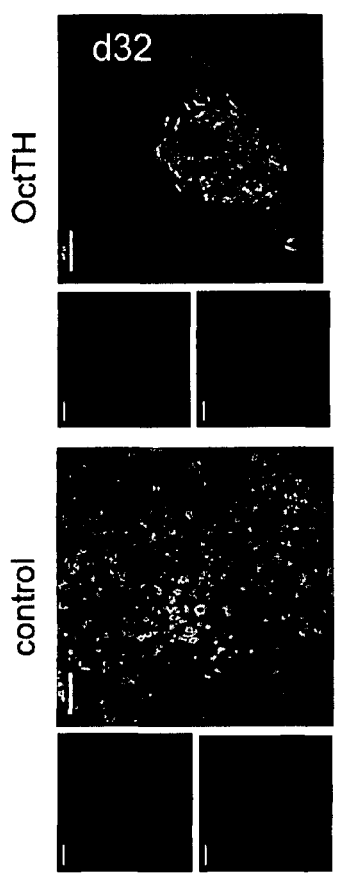

FIG. 7B: Substitution of Oct4-encoding virus by OctTH fusion protein.

Virus-substitution experiment as outlined in FIG. 7A exemplified by the transduction of OctTH fusion protein into Oct4-GFP MEFs. Substitution of Oct4-encoding virus by Oct4 fusion protein results in the formation of iPS colonies exhibiting ES morphology, Oct4-GFP fluorescence and SSEA1 immunoreactivity (upper panel). Control cells, treated with three viruses (Sox2, Klf4, cMyc) only, do not form colonies (lower panel). Photos were taken 32 days after viral transduction.

Figure 7C:
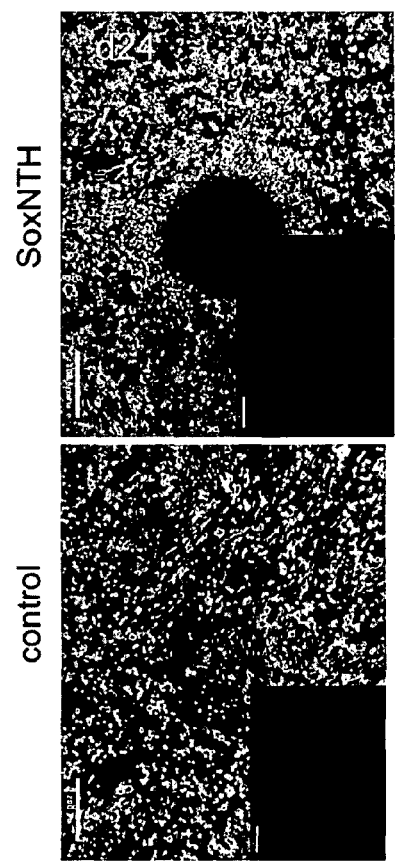

FIG. 7C: Substitution of Sox2-encoding virus by Sox2NTH fusion protein.

Virus-substitution experiment as outlined in FIG. 7A exemplified by the transduction of Sox2NTH fusion protein into Oct4-GFP MEFs. Substitution of Sox2-encoding virus by Sox2 fusion protein results in the formation of iPS colonies exhibiting ES morphology and Oct4-GFP fluorescence (upper panel). Control cells, treated with three viruses (Oct4, Klf4, cMyc) only, do not form colonies (lower panel). Photos were taken 24 days after viral transduction.

FIG. 8A: Schematic representation of an experiment aimed at reprogramming neural stem cells (NSCs) by OctTH fusion protein.

NSCs are plated and optionally transduced with viruses encoding up to two factors (Klf4, cMyc). Although NSCs do endogenously express cMyc, Klf4 and Sox2, additional overexpression of cMyc and Klf4 induced by viruses might enhance reprogramming. Thus, viral transduction is expected to enhance iPS derivation while not being essential. OctTH fusion protein is provided at day 1 as a recombinant cell-permeant protein diluted from a glycerol stock into NSC medium. From day 2 on OctTH is applied daily with protein transduction medium.

Figure 8B:
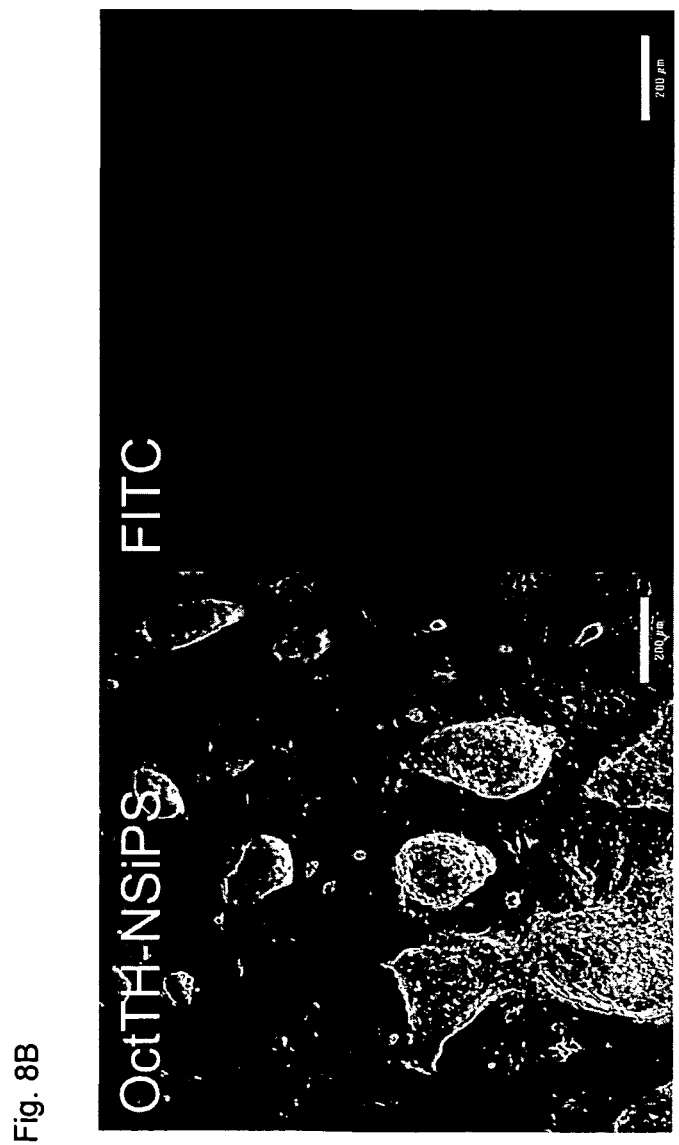

FIG. 8B: iPS clone derived from NSC cells by Oct4 fusion protein substitution.

According to the schematic representation in FIG. 8A MEFs were transduced with Klf4- and cMyc-encoding viruses together with a GFP-virus. Cells were cultivated in Oct4TH-containing media for 14 days. At day 16 colonies were picked and expanded. Brightfield and GFP channel photos of one clone is given demonstrating compact iPS morphology and inactivation of the viral GFP, indicative for efficient silencing of viral constructs.

EXAMPLES

The invention is further described by the following examples. It is, however, understood that the examples are not limiting and for illustrative purposes only.

Example 1

Generation of Transducible Versions of the Transcription Factors Oct4 and Sox2

The generation of transducible versions of the transcription factors Oct4 and Sox2 was conducted by cloning the cDNAs of both factors into the vector(s). The resulting expression constructs were transformed into an *Escherichia coli* expression strain and recombinant proteins were purified from the soluble fraction of bacterial lysates by Ni-(II)-affinity chromatography. Sox2NTH was well enriched and detected by a Sox2-specific antibody migrating at the calculated molecular weight of 40 kDa (FIG. 1C), whereas in the elution fraction of HTNSox2 additional contamination bands occurred in SDS-PAGE analysis, which were identified by an anti His-specific antibody, indicating premature translational termination (FIG. 1D). Sox2NTH was concentrated in a glycerol stock to a concentration of 3-4.5 µM.

Example 2

Analysis of Both Variants of Tagged Oct4 Regarding their Solubility and Stability It turned out that N-terminal tagged Oct4 (HTNOct4) resulted in a poor yield, whereas the C-terminal location of tags resulted in a strongly increased expression yield. Since Pou5f1 includes an internal NLS-encoding sequence (Pan et al., 2004) we anticipated that the exogenous NLS encoded by the vector is dispensable. Oct4TH was purified from the soluble fraction of *E. coli* lysates by Ni-(II)-affinity chromatography, was identified by an Oct4-specific antibody at the molecular weight of about 48 kDa and could be enriched in a glycerol stock to a concentration of 2-2.5 µM (FIG. 1E). The stability of both Oct4TH and Sox2NTH was analyzed after diluting the stock in cell culture medium and under cell culture conditions of 37° C. In normal ES cell medium most of the recombinant proteins Oct4TH and Sox2NTH was lost already after 1 hour predominantly due to precipitation, however, the solubility could be markedly enhanced by the addition of Albumax (a lipid rich serum). Based on these observations, Oct4TH and Sox2NTH proteins were supplied in Albumax-supplemented medium every day (FIG. 1F). Investigations revealed that out of the various fusion proteins investigated, Oct4TH and Sox2NTH turned out to exhibit the best combination of purity, solubility and stability.

Example 3

Assessment of the Functionality of the Recombinant Proteins Oct4TH and Sox2NTH First the ability of the purified proteins to specifically bind to DNA was determined. For that an electrophoretic mobility shift assay (EMSA) employing a particular octamer-sox composite element that was recently identified to be an Oct4-Sox2 target sequence within the Nanog regulatory region (Kuroda et al., 2005; Rodda et al., 2005) was performed. The EMSA shows that both recombinant fusion proteins, Oct4TH and Sox2NTH, individually bind to the target sequence (FIG. 2, lane 2, 6). The binding of Oct4 to the labelled probe could be competed by a 500-fold excess of unlabelled probe (FIG. 2, lane 3). The specificity of the protein/DNA-complexes was assessed by the addition of specific antibodies. Indeed, we observed that the Oct4/DNA and Sox2/DNA complexes were shifted by Oct4- and Sox2-specific antibodies, respectively, resulting in super shifted bands (FIG. 2, lane 4, 7). The Oct4/DNA-complex was not bound by Sox2 antibody, confirming the specificity of the super shift (FIG. 2, lane 5). After incubating both recombinant proteins with the target sequence a slower migrating band that was identified as an Oct4/Sox2/DNA ternary complex (FIG. 2, lane 9) was observed. Additionally, a strong band at the height of the Oct4/DNA complex was observed. Both complexes were shifted by an Oct4 specific antibody (lane 9) but not by a Sox2 specific antibody (lane 10).

Example 4

Assessment of the Cell Permeability of the Recombinant Oct4TH and Sox2NTH Proteins For monitoring the localization of the proteins during cellular uptake in living cells Rhodamine labelled fractions of purified proteins were used, referred to as R-Oct4TH and R-Sox2NTH. Labelled proteins were applied for 30 minutes on CV1 cells. This cell type was chosen because of the large cytoplasm in relation to the size of the nucleus, which is helpful in visualizing the path of the proteins through the cell (Tunnemann et al., 2006; Wadia et al., 2004). After removing extracellularly bound protein by heparin a punctuate pattern presumably resulting from endosomal uptake which persisted for at least 24 hours was observed. In the case of Sox2NTH transduction this pattern was observed in 85±5% of the cells. Oct4TH transduction turned out to be even stronger since 97±1% of Oct4-transduced cells displayed the characteristic vesicular staining. This pattern is typical for cell-permeant proteins after cellular uptake as has been reported in numerous studies (Tunnemann et al., 2006; Wadia et al., 2004; Peitz et al., 2007). It has been reported that the majority of the internalized protein is initially located in endosomal vesicles and that only a low percentage is released into the cytosol and subsequently translocated into the nucleus (Tunnemann et al., 2006). Optical sections through the cell in different layers were performed employing the Apotome sectioning device to confirm the localization of the endosomally released labelled proteins in the nucleus as well. As a result, it was possible to show nuclear localization. This indicates, that Oct4TH and Sox2NTH are internalized by cells and are able to translocate into the nucleus.

In order to analyse potential deleterious effects of the transduction procedure as such proliferation analysis of the transduced cells was carried out. It turned out that both Oct4- as well as Sox2-treated cells proliferated with a similar potential as untreated control cells.

Example 5

Activity of the Recombinant Proteins in ES Cells

After demonstrating that Sox2NTH and Oct4TH are translocated into fibroblast cells it was aimed at analyzing the activity of the recombinant proteins in ES cells. For that ES cells were incubated for 5 days in the presence of the transducible proteins (FIGS. 4A, B). It was observed that application of each factor on its own as well as the combination of both resulted in increasing numbers of highly compacted ES cell colonies with distinct borders. Moreover, these colonies exhibited a strong alkaline phosphatase (AP) activity, a pluripotency-associated marker (FIG. 4A). Though total number of colonies is decreasing under high protein concentration to about the half (data not shown), there is a clear shift to more undifferentiated ES colonies upon transduction of Oct4 and Sox2. Quantification revealed that cultures kept under control conditions displayed 14% highly compacted colonies whereas increasing concentrations of Oct4TH to up to 100 µM resulted in about 68% highly compacted colonies and 56% in the case of Sox2NTH 150 µM (FIG. 4B). In order to analyze whether the transduction procedure has a deleterious effect on the viability of the cells transduced cells were analyzed by flow cytometry five days after transduction. It was found that all protein concentrations used did result in only negligible differences between the number of living cells in comparison to untreated cells (FIG. 4C).

Example 6

Assessment of the Functionality of Transducible Oct4 and Sox2 in ES Cells at a Molecular Level For this the ability of the transducible factors to compensate the knock down (k.d.) of the respective gene was explored. First the efficiency of Pou5f1 and Sox2 k.d. by introducing short interfering RNAs (siRNA) into ES cells in the presence of LIF was analyzed. siRNA sequences directed against Pou5f1 and Sox2 used in this assay were reported to be functional and specific for each target gene (Hay et al., 2004; Ivanova et al., 2006). As a control, a non-target siRNA was used. Western blot analysis showed that protein levels of both target factors were decreased to about 30% of the normal expression level (FIG. 5A). Time course analysis indicated that the k.d. was stable for at least three days. Immunofluoresence confirmed these findings by demonstrating that Oct4 was down regulated in up to 80% of the colonies, and Sox2 in about 50% (FIGS. 5B, C). According to RT PCR analysis, an almost complete down-regulation of Pou5f1 and a 40% down-regulation of Sox2 (FIGS. 5D, E) was observed. With respect to cellular growth different changes upon knocking down either Pou5f1 or Sox2 were observed. Compared to untreated control cells Pou5f1 k.d. resulted in the formation of 70% less colonies and many detached cells, indicative of massive cell death (FIGS. 6A, B). Sox2 k.d. caused, in addition to decreased colony formation, strong differentiation into a presumably epithelial-like phenotype (FIGS. 6A, C). Taking together these observations demonstrated that k.d. of both Pou5f1 and Sox2, respectively, is highly efficient and result in a characteristic phenotypical change of the cultured cells.

Example 7

Figure 6:
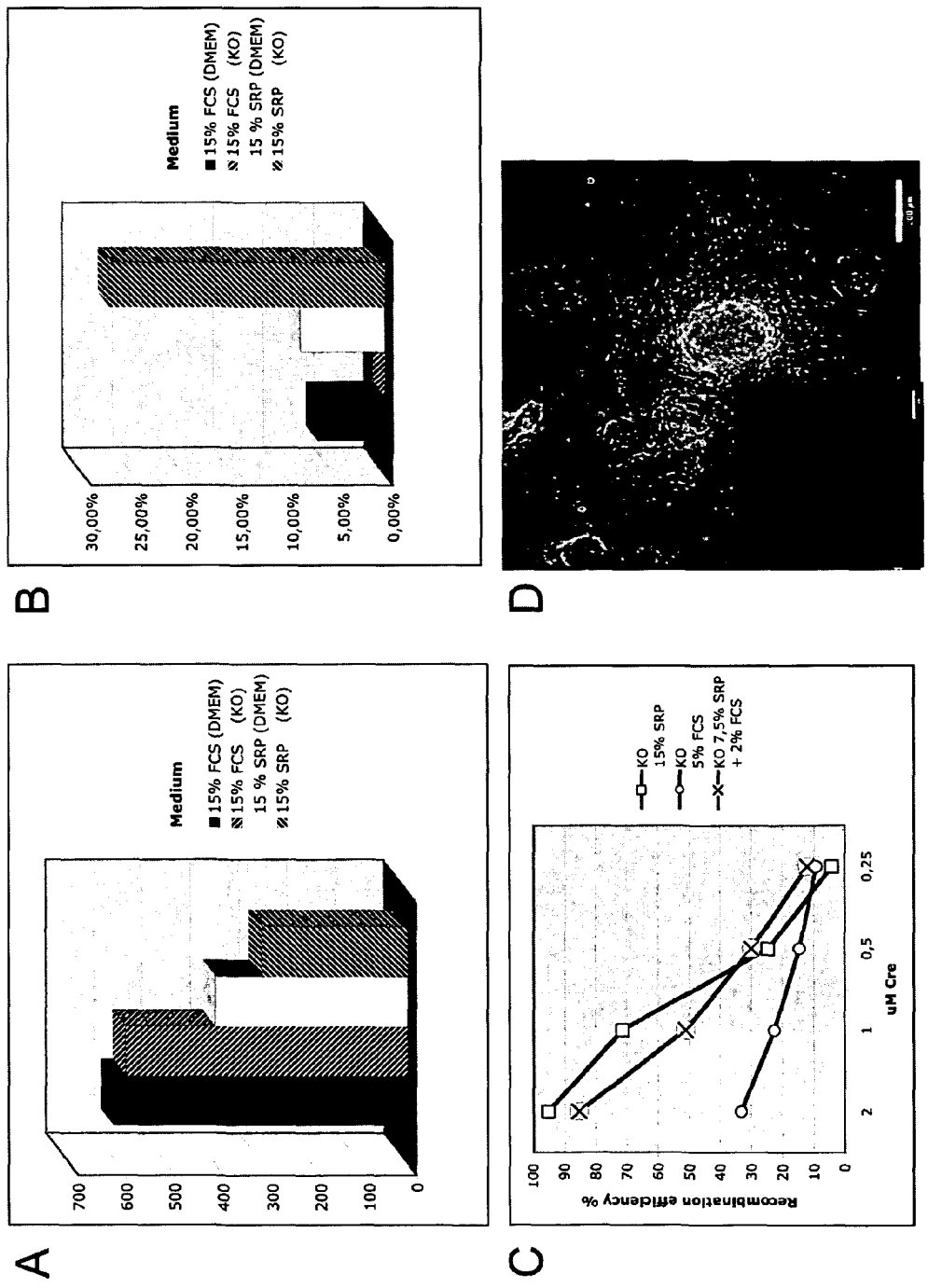

Introducing the Down Regulated Factors to the Treated Cells by Protein Transduction It was analyzed whether these changes, induced by RNAi k.d. of Pou5f1 and Sox2, could be rescued by introducing the down regulated factors to the treated cells by protein transduction. Oct4TH and Sox2NTH were introduced 24 hours after beginn of the k.d. The experiment was stopped 48 hours after beginn of the k.d. This period of time turned out to be sufficient for the sustained and efficient k.d. (FIG. 5A). Oct4TH transduction resulted in doubling of colony numbers and formation of larger colonies (FIGS. 6A, B). Sox2NTH delivery did not result in a significant change of the colony numbers, but yielded an increased percentage of colonies exhibiting non-differentiated morphology (FIGS. 6A, C). RNA was isolated from treated cells and expression levels of different pluripotency markers were analyzed by quantitative RT-PCR. Pou5f1 transcription was down regulated after transfection of specific siRNA about 40-fold as compared to untreated control cells (FIG. 6D), however, only a slight reduction of Sox2 and Nanog transcript levels was observed. After adding cell-permeant Oct4TH fusion protein to the culture down-regulation of Pou5f1 turned out to be compensated to 70%. In Sox2 siRNA treated cells the Sox2 transcript level was 2-fold less than in control cells (FIG. 6 E). At the same time expression levels of Pou5f1 and Nanog were about 8-fold down regulated, which is consistent with other studies reporting Sox2 don-regulation (Chew et al., 2005; Masui et al., 2007). This down-regulation was compensated significantly by the application of Sox2NTH to the culture. The transduction of Sox2NTH could prevent the down-regulation of Pou5f1 and Nanog for about 30 to 60%. The rescue of Sox2 k.d. was only slight, this could be due to the loss of the interaction partner Oct4. However, the ability to rescue the expression of Pou5f1 and Nanog shows the transactivation capacity of Sox2NTH. Taking together these findings demonstrate that transducible Oct4 and Sox2 are powerful tools for the manipulation of the pluripotency transcriptional machinery without genetic interference.

Example 8

Fusion Protein-Induced Derivation of iPS Colonies from MEFs

In order to identify the optimal concentration of fusion proteins one viral vector was substituted by the corresponding fusion protein. OctGFP-MEFs were transduced with Sox, klf and c-Myc by retroviral infection at day 0. At day 1 the medium was changed to knock-out based OctTH-dialysate (see schematic presentation in FIG. 7A). The dialysate was supplemented with β-Mercaptoethanol (100 µM), NEAA, Glutamine, Insulin-Transferrin-selenite, Albumax (5 mg/ml), 5% fetal calf serum and 1000 u/ml Lif, heat-shocked and applied to cell culture. At day 5 cells were splitted onto irradiated MEFs and the composition of the transduction medium changed. Now the knock-out based dialysate was supplemented with β-Mercaptoethanol (100 µM), NEAA, Glutamine, Albumax (5 mg/ml), 15% serum-replacement and 1000 u/ml Lif. Protein transduction was continued until day 14. First colonies emerged at day 9. Cells were analyzed for GFP fluoresence and stained for pluripotency markers such as SSEA1 (FIGS. 7B,C)

Example 9

Fusion Protein-Induced Derivation of iPS Colonies from Neural Stem Cells (NSCs)

NSCs were transduced with Klf4, c-Myc and GFP by retroviral infection in NCS culture medium at day 0. Retroviral transfection is optional since NSCs endogenously express Sox2, Klf4 and cMyc. Additional overexpression induced by viruses is not necessary but may enhance the efficacy of iPS derivation. Cells were further cultivated in NSC medium supplemented with Albumax (final conc. 5 mg/ml) and a dilution (1:20) of OctTH fusion protein from a glycerol-stock for two days as schematically given in FIG. 8A. At day 3 cells were splitted onto irradiated MEFs and the medium was changed to F 12-based OctTH-dialysate. The dialysate was supplemented with (3-mercaptoethanol (100 µM), NEAA, Insulin-Transferrin-selenite, Albumax (final conc. 5 mg/ml), 7.5% serum replacement, 2% fetal calf serum and 1000 u/ml Lif, heat-shocked and applied to cell culture. Cells were cultivated in OctTH containing medium for 14 days, thereafter the medium was changed to standard ES cell culture medium. First colonies emerged at day 7. At day 16 colonies were picked and expanded. Cells were analyzed for GFP fluorescence and stained for pluripotency markers such as SSEA1 (FIG. 8B).

Material and Methods

The following methods have been used within the examples of the present invention. It is, however, possible to apply all methods known to a person skilled in the art as suitable for the inventive purpose.

Construction of Expression Plasmids pTriEx-HTNC generated by Peitz et al. 2002 was used as a basis vector. The NLS-Cre encoding fragment was deleted by restriction hydrolysis. NLS-Pou5f1 including the respective restriction sites (FIGS. 1A, B) was generated by PCR and inserted into pTriEx-HT by using SpeI and XhoI sites and by that generating the vector containing Pou5f1 and cDNA. The vector with HTNSox2 was generated by amplifying Sox2-encoding cDNA by PCR and cloning it into the vector using AvrII and NheI sites.

Sequences encoding C-terminal tags were ordered as a double stranded oligo nucleotide (Invitrogen®) and inserted into the vector by using NheI and XhoI sites. For the deletion of the NLS-encoding fragment an EcoRI restriction hydrolysis was performed. The vector was purified via agarose gel electrophoresis and religated. All PCR-generated as well as chemically synthesized sequences were verified by sequencing.

Protein Expression and Purification

Expression plasmids were transformed into *E. coli* BL21 (DE3) gold strain (Stratagene) by a 30° C. heat shock and incubated for 1 h in S.O.C medium at 30° C. Transformed bacteria were inoculated over night at 30° C. and 140 rpm in LB medium with 50 µg/ml carbenicillin. For protein expression over night culture was diluted 1:20 into TB medium (terrific broth)/50 µg/ml ampicillin, 0.5% glucose and incubated at 37° C. and 110 rpm until $OD_{600}$ reached 1.5. Protein expression was induced by IPTG at a final concentration of 0.5 mM. Cells were harvested by centrifugation and pellets stored at −20° C.

For purification of His-tagged proteins, pellets were thawed and resuspended in lysis buffer (50 mM $Na_2HPO_4$, 5 mM tris (pH 7.8)/500 mM NaCl/10 mM imidazol) 20 ml per 1 l expression culture. Cells were lysed by application of 1 mg/ml lysozym (Sigma), 10-15 U/µl Benzonase (Novagen), and final sonication. After centrifugation (12000 rpm, 20 min) cleared lysate was incubated with Ni-NTA agarose beads (Qiagen) (1 ml slurry for 1 l bacterial expression culture) for 1 h rotating at 4° C. Slurry was packed onto a column and washed with 8 column volumes (CV) of wash buffer (50 mM $Na_2HPO_4$, 5 mM Tris (pH 7.8), 500 mM NaCl, 80 mM imidazol for Sox2NTH and 90 mM for Oct4TH). Protein was eluted with 3 CV elution buffer (50 mM $Na_2HPO_4$, 5 mM Tris (pH 7.8), 500 mM NaCl, 250 mM imidazol). For the preparation of storage solutions the purified Sox2NTH and Oct4TH fractions were transferred to a glycerol buffer glycerol buffer (50% glycerol, 1M NaCl, 1 mM DTT, 1 mM EDTA) by dialysis. Proteins could be stored at −20° C. and diluted into the cell culture medium up to 1:20.

Western Blot

Samples were separated on 10% SDS-gels and blotted on nitrocellulose membrane (Roth). For identification of recombinant proteins Oct 3/4 (sc-5279) (Santa Cruz Biotechnology), Sox2 (ab15830) (Abcam), Stat-3 (Cell Signalling Technology), anti-His HRP conjugate (Qiagen®) antibodies were employed. Anti mouse IgG and anti rabbit IgG, both HRP-linked (Cell Signalling Technology) were used as secondary antibodies. Signal was detected by SuperSignal West Pico or Femto Chemiluminescent Substrate (PIERCE).

EMSA

EMSA was performed with LightShift Chemiluminescent EMSA kit (Pierce) according to manufactures instructions. Protein samples were taken from the glycerol stock (1 µl) and incubated with 20 fmol 5"-biotin-labelled double stranded target sequence DNA oligonucleotides (Rodda et al., 2005) and binding buffer (10 mM tris, 50 mM KCl, 1 mM DTT, poly(dI-dC)). For the super shift specific antibodies were added, 4 µl Oct 3/4 (sc-5279) (Santa Cruz Biotechnology) or 8 µl Sox2 (ab15830) (Abcam). Total sample volume was 20 µl. Samples were incubated for 20 min at room temperature. After that sample buffer was added and the samples were separated on 6% native acrylamid gel in 0.5×TBE and blotted on a positively charged nylon membrane (Roche). Signals were detected with the CCD camera of a ChemiDoc XRS documentation system (Biorad).

Cell Culture

Oct4-GiP mouse ES cells (Ying et al., 2002) were cultured on gelatin-coated dishes in high glucose D-MEM (Invitrogen) with 15% FCS, 1% non-essential amino acids, 1 mM sodium pyruvate, 2 mM L-glutamine 100 µM (3-mercaptoethanol and 1000 U/ml LIF (Chemicon) or Advanced D-MEM (Invitrogen) with 5% FCS, 2 mM L-glutamine, 100 µM β-mercaptoethanol and 1000 U/ml LIF.

Protein Transduction Conditions

Culture media for transduction experiments were prepared by mixing glycerol stocks (concentration were approximately 3 µM for Sox2NTH and 1.5 µM for Oct4TH) of the proteins 1:20 or 1:50 with Advanced D-MEM medium (Invitrogen) supplemented with 5% FCS, 0.5% Albumax II, 0.5% ITS, 0.5% Sodium Pyruvat, 0.5% non-essential amino acids, 1% glutamine, 100 µM β-mercaptoethanol. The mixture was incubated in a water bath for 1 h at 37° C. and cleared from precipitations by centrifugation (5 min at 4000 rpm) and sterile filtration. Protein content of the medium was analyzed by western blotting. For alkaline phosphatase staining Oct4 GiP cells (Ying et al., 2002) were plated at low density (500 cells/well of a 24 well plate) on gelatine. Transduction medium was prepared as described before. Protein stocks were diluted maximum 1:20 with medium. Corresponding volumes of glycerol buffer was added to cell culture media of low protein concentrated as well as untreated control cells in order to provide equal experimental conditions. Medium was changed every day. After 5 days of culture cells were fixed with 4% PFA and stained on alkaline phosphatase (Vector Laboratories).

Rhodamine Labelling

Purified proteins are transferred over a PD-10 desalting column (GE Healthcare) from the eluate to an imidazol-free buffer (500 mM NaCl, 20 mM Hepes, pH 7.4) and incubated on ice for 2 h with labelling reagent NHS-Rhodamine (Pierce Biotechnology) according to manufacturer's instructions. Unbound Rhodamine was eliminated by passing the sample over a PD-10 column again and eluting with Advanced D-MEM (Invitrogen) and afterwards supplementing with 5% FCS (Gibco) and 0.5% Albumax (Gibco). Protein was incubated at 37° C. for 1 h and centrifuged 5 min at 4000 rpm to get rid of insoluble protein. After that protein was added for 30 min on CV-1 cells stained with Hoechst (Molecular Probes). After removal of the protein a Heparin (Sigma) wash (0.5 mg/ml in PBS) was performed to remove uninternalized protein.

Growth Curve $5 \cdot 10^4$ NIH 3T3 cells were plated per well of a 12 well plate. Cells were treated with transduction media described above and split every 3-4 days. Cell count was taken and $5 \cdot 10^4$ cells/well plated again. Experiment was performed in triplicate.

FACS Analysis

Cells were harvested by treating the cells 5 min with Triple Express (Invitrogen) and separated by repetitive pipetting. Single cell suspension was sorted by LSRII analytical flow cytometer (BD Biosciences). Dead cells were excluded by staining with Hoechst 33258 (Invitrogen).

RNAi

Oct4 GiP ES cells were plated on 6 well plates $2 \cdot 10^5$ cells/well in 2 ml K.O. D-MEM (Invitrogen) medium with 15% serum replacement on gelatin. Immediately after plating cells were transfected with siRNA using Lipofectamine 2000 (Invitrogen). For Pou5f1 k.d. 100 nM siRNA in 250 µl were mixed with 8 µl Lipofectamine reagent in 250 µl Opti-MEM for each well. For Sox2 k.d. 100 nM siRNA in 500 µl were mixed with 16 µl Lipofectamine reagent in 500 µl Opti-MEM medium for each well. Medium was changed 24 h after beginning of transfection.

Double stranded siRNA oligonucleotides were ordered from Qiagen. siRNA Sequences were published for Pou5f1 by Hay 04, and for Sox2 by Ivanova et al 06. AllStars Negative Control siRNA from Qiagen was used as a negative control.

RNA Preparation and Quantitative RT PCR

Total RNA was isolated by RNA purification system (Invitrogen). cDNA was prepared by iscript cDNA synthesis Kit (Biorad). Quantitative real time PCR (qRT-PCR) was performed with an I Cycler (Biorad) using SyberI-green detection method. β-Actin was used for normalization. Each sample was analyzed in triplicate.

```
Primer sequences:
b-Actin_forw:
                                    (SEQ ID NO: 9)
5'-CTGGCTCCTAGCACCATGAA-3' b-Actin_rev:
                                    (SEQ ID NO: 10)
5'-GCCGGACTCATCGTACTCCT-3'

Pou5f1_for:
                                    (SEQ ID NO: 11)
5'-CCCTGCAGAAGGAGCTAGAAC-3'

Pou5f1_rev:
                                    (SEQ ID NO: 12)
5'-CTTAAGGCTGAGCTGCAAGG-3'

Sox2_forw:
                                    (SEQ ID NO: 13)
5'-CCCCTTTTATTTTCCGTAGTTGTAT-3'

Sox2_rev:
                                    (SEQ ID NO: 14)
5'-TCAAACTGTGCATAATGGAGTAAAA-3'

Nanog_for:
                                    (SEQ ID NO: 15)
5'-AGGGTCTGCTACTGAGATGCTCTG-3'

Nanog_rev:
                                    (SEQ ID NO: 16)
5'-CAACCACTGGTTTTTCTGCCACCG-3'
```

REFERENCES

Avilion, A. A., Nicolis, S. K., Pevny, L. H., Perez, L., Vivian, N., and Lovell-Badge, R. (2003). Multipotent cell lineages in early mouse development depend on SOX2 function. Genes & development 17, 126-140.

Bernstein, B. E., Mikkelsen, T. S., Xie, X., Kamal, M., Huebert, D. J., Cuff, J., Fry, B., Meissner, A., Wernig, M., Plath, K., et al. (2006). A bivalent chromatin structure marks key developmental genes in embryonic stem cells. Cell 125, 315-326.

Boer, B., Kopp, J., Mallanna, S., Desler, M., Chakravarthy, H., Wilder, P. J., Bernadt, C., and Rizzino, A. (2007). Elevating the levels of Sox2 in embryonal carcinoma cells and embryonic stem cells inhibits the expression of Sox2: Oct-3/4 target genes. Nucleic acids research 35, 1773-1786.

Boyer, L. A., Lee, T. I., Cole, M. F., Johnstone, S. E., Levine, S. S., Zucker, J. P., Guenther, M. G., Kumar, R. M., Murray, H. L., Jenner, R. G., et al. (2005). Core transcriptional regulatory circuitry in human embryonic stem cells. Cell 122, 947-956.

Boyer, L. A., Plath, K., Zeitlinger, J., Brambrink, T., Medeiros, L. A., Lee, T. I., Levine, S. S., Wernig, M., Tajonar, A., Ray, M. K., et al. (2006). Polycomb complexes repress developmental regulators in murine embryonic stem cells. Nature 441, 349-353.

Braun, P., Hu, Y., Shen, B., Halleck, A., Koundinya, M., Harlow, E., and LaBaer, J. (2002). Proteome-scale purification of human proteins from bacteria. Proceedings of the National Academy of Sciences of the United States of America 99, 2654-2659.

Chew, J. L., Loh, Y. H., Zhang, W., Chen, X., Tam, W. L., Yeap, L. S., Li, P., Ang, Y. S., Lim, B., Robson, P., and Ng, H. H. (2005). Reciprocal transcriptional regulation of Pou5f1 and Sox2 via the Oct4/Sox2 complex in embryonic stem cells. Molecular and cellular biology 25, 6031-6046.

Dailey, L., Basilico, C. (2001). Coevolution of HMG domains and homeodomains and the generation of transcriptional regulation by Sox/POU complexes. J Cell Physiol. 186, 315-328.

Dietz, G. P., and Bahr, M. (2004). Delivery of bioactive molecules into the cell: the Trojan horse approach. Molecular and cellular neurosciences 27, 85-131.

Frankel, A. D., and Pabo, C. O. (1988). Cellular uptake of the tat protein from human immunodeficiency virus. Cell 55, 1189-1193.

Glover, D. J., Lipps, H. J., and Jam, D. A. (2005). Towards safe, non-viral therapeutic gene expression in humans. Nat Rev Genet. 6, 299-310.

Green, M., and Loewenstein, P. M. (1988). Autonomous functional domains of chemically synthesized human immunodeficiency virus tat trans-activator protein. Cell 55, 1179-1188.

Hay, D. C., Sutherland, L., Clark, J., and Burdon, T. (2004). Oct-4 knockdown induces similar patterns of endoderm and trophoblast differentiation markers in human and mouse embryonic stem cells. Stem cells (Dayton, Ohio) 22, 225-235.

Hough, S. R., Clements, I., Welch, P. J., and Wiederholt, K. A. (2006). Differentiation of mouse embryonic stem cells after RNA interference-mediated silencing of OCT4 and Nanog. Stem cells (Dayton, Ohio) 24, 1467-1475.

Ivanova, N., Dobrin, R., Lu, R., Kotenko, I., Levorse, J., DeCoste, C., Schafer, X., Lun, Y., and Lemischka, I. R. (2006). Dissecting self-renewal in stem cells with RNA interference. Nature 442, 533-538.

Joliot, A., and Prochiantz, A. (2004). Transduction peptides: from technology to physiology. Nature cell biology 6, 189-196.

Kaplan, I. M., Wadia, J. S., and Dowdy, S. F. (2005). Cationic TAT peptide transduction domain enters cells by macropinocytosis. J Control Release 102, 247-253.

Kuroda, T., Tada, M., Kubota, H., Kimura, H., Hatano, S. Y., Suemori, H., Nakatsuji, N., and Tada, T. (2005). Octamer and Sox elements are required for transcriptional cis regulation of Nanog gene expression. Molecular and cellular biology 25, 2475-2485.

Landry, J. R., S. Kinston, K. Knezevic, M. de Bruijn, N. Wilson, W. T. Nottingham, M. Peitz, F. Edenhofer, J. E. Pimanda, K. Ottersbach and B. Göttgens. (2008) Runx genes are direct targets of Scl/Tal1 in the yolk sac and fetal liver. Blood 15, 3005-3014

Loh, Y. H., Wu, Q., Chew, J. L., Vega, V. B., Zhang, W., Chen, X., Bourque, G., George, J., Leong, B., Liu, J., et al. (2006). The Oct4 and Nanog transcription network regulates pluripotency in mouse embryonic stem cells. Nature genetics 38, 431-440.

Lowry, W. E., Richter, L., Yachechko, R., Pyle, A. D., Tchieu, J., Sridharan, R., Clark, A. T., Plath, K. (2008). Generation of human induced pluripotent stem cells from dermal fibroblasts. Proc Natl Acad. Sci. 26, 2883-2888

Maherali, N., Sirdharan, R., Xie, W., Utikal, J., Eminli, S., Arnold, K., Sadtfld, M., Yachechenko, R., Techieu, J., Jaenisch, R., Plath, K., and Hochedlinger, K. (2007). Directly reprogrammed fibroblasts show global epigenetic remodelling and widespread tissue contribution. Cell stem cell 1, 55-70.

Masui, S., Nakatake, Y., Toyooka, Y., Shimosato, D., Yagi, R., Takahashi, K., Okochi, H., Okuda, A., Matoba, R., Sharov, A. A., et al. (2007). Pluripotency governed by Sox2 via regulation of Oct3/4 expression in mouse embryonic stem cells. Nature cell biology 9, 625-635.

Munsie, M. J. et al., Curr. Biol. 10, 989-992, (2000)

Nakagawa, M., Koyanagi, M., Tanabe, K., Takahashi, K., Ichisaka, T., Aoi, T., Okita, K., Mochiduki, Y., Takizawa, N., and Yamanaka, S. (2008). Generation of induced pluripotent stem cells without Myc from mouse and human fibroblasts. Nature biotechnology 26, 101-106.

Nichols, J., Zevnik, B., Anastassiadis, K., Niwa, H., Klewe-Nebenius, D., Chambers, I., Scholer, H., and Smith, A. (1998). Formation of pluripotent stem cells in the mammalian embryo depends on the POU transcription factor Oct4. Cell 95, 379-391.

Nishimoto, M., Fukushima, A., Okuda, A., and Muramatsu, M. (1999). The gene for the embryonic stem cell coactivator UTF1 carries a regulatory element which selectively interacts with a complex composed of Oct-3/4 and Sox-2. Molecular and cellular biology 19, 5453-5465.

Niwa, H. (2007). How is pluripotency determined and maintained? Development (Cambridge, England) 134, 635-646.

Niwa, H., Miyazaki, J., and Smith, A. G. (2000). Quantitative expression of Oct-3/4 defines differentiation, dedifferentiation or self-renewal of ES cells. Nature genetics 24, 372-376.

Niwa, H., Burdon, T., Chambers, I, Smith, A. (1998). Self-renewal of pluripotent embryonic stem cells is mediated via activation of STATS. Genes Dev. 1, 2048-2060.

Nolden, L., F. Edenhofer, S. Haupt, F. T. Wunderlich, H. Siemen & O. Brüstle. (2006). Site specific recombination in human ES cells induced by cell permeable Cre recombinase. Nature Methods 3, 461-467.

Okita, K., Ichisaka, T., and Yamanaka, S. (2007). Generation of germline-competent induced pluripotent stem cells. Nature 448, 313-317.

Okumura-Nakanishi, S., Saito, M., Niwa, H., and Ishikawa, F. (2005). Oct-3/4 and Sox2 regulate Oct-3/4 gene in embryonic stem cells. The Journal of biological chemistry 280, 5307-5317.

Pan, G., Qin, B., Liu, N., Scholer, H. R., and Pei, D. (2004). Identification of a nuclear localization signal in OCT4 and generation of a dominant negative mutant by its ablation. The Journal of biological chemistry 279, 37013-37020.

Park, I. H., Zhao, R., West, J. A., Yabuuchi, A., Huo, H., Ince, T. A., Lerou, P. H., Lensch, M. W., Daley, G. Q. (2008). Reprogramming of human somatic cells to pluripotency with defined factors. Nature 10, 141-146

Patsch, C. and F. Edenhofer. (2007). Conditional Mutagenesis by cell-permeable proteins: potential, limitations and prospects, Handb. Exp. Pharmacol. 178, 203-232.

Peitz, M., Pfannkuche, K., Rajewsky, K., and Edenhofer, F. (2002). Ability of the hydrophobic FGF and basic TAT peptides to promote cellular uptake of recombinant Cre recombinase: a tool for efficient genetic engineering of mammalian genomes. Proceedings of the National Academy of Sciences of the United States of America 99, 4489-4494.

Pesce, M., and Scholer, H. R. (2001). Oct-4: gatekeeper in the beginnings of mammalian development. Stem cells (Dayton, Ohio) 19, 271-278.

Rodda, D. J., Chew, J. L., Lim, L. H., Loh, Y. H., Wang, B., Ng, H. H., and Robson, P. (2005). Transcriptional regulation of nanog by OCT4 and SOX2. The Journal of biological chemistry 280, 24731-24737.

Smith, A. G. (2001). Embryo-derived stem cells: of mice and men. Annual review of cell and developmental biology 17, 435-462.

Tada, M., Tada, T., Lefebvre, L., Barton, S. c. & Surani, M. A. EMBO J. 16, 6510-6520 (1997) Takahashi, K., Okita, K., Nakagawa, M., and Yamanaka, S. (2007). Induction of pluripotent stem cells from fibroblast cultures. Nature protocols 2, 3081-3089.

Takahashi, K., and Yamanaka, S. (2006). Induction of pluripotent stem cells from mouse embryonic and adult fibroblast cultures by defined factors. Cell 126, 663-676.

Tokuzawa, Y., Kaiho, E., Maruyama, M., Takahashi, K., Mitsui, K., Maeda, M., Niwa, H., and Yamanaka, S. (2003). Fbx15 is a novel target of Oct3/4 but is dispensable for embryonic stem cell self-renewal and mouse development. Molecular and cellular biology 23, 2699-2708.

Tomioka, M., Nishimoto, M., Miyagi, S., Katayanagi, T., Fukui, N., Niwa, H., Muramatsu, M., and Okuda, A. (2002). Identification of Sox-2 regulatory region which is under the control of Oct-3/4-Sox-2 complex. Nucleic acids research 30, 3202-3213.

Tunnemann, G., Martin, R. M., Haupt, S., Patsch, C., Edenhofer, F., and Cardoso, M. C. (2006). Cargo-dependent mode of uptake and bioavailability of TAT-containing proteins and peptides in living cells. Faseb J 20, 1775-1784.

Wadia, J. S., Stan, R. V., and Dowdy, S. F. (2004). Transducible TAT-HA fusogenic peptide enhances escape of TAT-fusion proteins after lipid raft macropinocytosis. Nat Med 10, 310-315.

Wernig, M., Meissner, A., Cassady, J. P., Jaenisch R. (2008). c-Myc is dispensable for direct reprogramming of mouse fibroblasts. Cell Stem Cell 10, 10-12.

Wernig, M., Meissner, A., Foreman, R., Brambrink, T., Ku, M., Hochedlinger, K., Bernstein, B. E., and Jaenisch, R.

(2007). In vitro reprogramming of fibroblasts into a pluripotent ES-cell-like state. Nature 448, 318-324.

Wilmut, I., Sci. Am. 279, 58-63 (1998)

Ying, Q. L., Nichols, J., Chambers, I., and Smith, A. (2003). BMP induction of 1d proteins suppresses differentiation and sustains embryonic stem cell self-renewal in collaboration with STAT3. Cell 115, 281-292.

Ying, Q. L., Nichols, J., Evans, E. P., and Smith, A. G. (2002). Changing potency by spontaneous fusion. Nature 416, 545-548.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science (New York, N.Y. 318, 1917-1920.

Yuan, H., Corbi, N., Basilico, C., and Dailey, L. (1995). Developmental-specific activity of the FGF-4 enhancer requires the synergistic action of Sox2 and Oct-3. Genes & development 9, 2635-2645.

SEQUENCE LISTING

Free Text Information

SEQ ID NO: 1 Fusion protein Oct4NTH
SEQ ID NO: 2 Fusion protein Oct4TH
SEQ ID NO: 3 Fusion protein HTNOct4
SEQ ID NO: 4 Fusion protein HTOCt4
SEQ ID NO: 5 Fusion protein Sox2NTH
SEQ ID NO: 6 Fusion protein Sox2TH
SEQ ID NO: 7 Fusion protein HTNSox2
SEQ ID NO: 8 Fusion protein HTSox2
SEQ ID NO: 9 PCR primer b-Actin_forw
SEQ ID NO: 10 PCR primer b-Actin_rev
SEQ ID NO: 11 PCR primer Pou5f1_for
SEQ ID NO: 12 PCR primer Pou5f1_rev
SEQ ID NO: 13 PCR primer Sox2_forw
SEQ ID NO: 14 PCR primer Sox2_rev
SEQ ID NO: 15 PCR primer Nanog_for
SEQ ID NO: 16 PCR primer Nanog_rev
SEQ ID NO: 17 Excerpt of coding region of vector pSESAME-N
SEQ ID NO: 18 Excerpt of coding region of vector pSESAME-C
SEQ ID NO: 19 nuclear localisation signal
SEQ ID NO: 20 coding sequence for nuclear localisation signal
SEQ ID NO: 21 basic peptide of HIV-1 TAT
SEQ ID NO: 22 coding sequence for basic TAT peptide

The invention claimed is:

1. A Fusion protein comprising:
   a) a protein transduction domain (PTD) comprising 6 to 12 basic amino acids; and
   b) at least one transcription factor, wherein said transcription factor is a stem cell factor.

2. The fusion protein of claim 1, wherein the PTD further comprises hydrophobic amino acids.

3. The fusion protein of claim 1, wherein the PTD further comprises at least one of TAT, Penetratin, HSV-VP22, Transportan, K-FGF, Oligoarginine, Arg-9, and peptides consisting of combinations of Arginine and Lysine residues.

4. The fusion protein of claim 1, wherein the PTD is comprised of no more than 20 amino acids.

5. The fusion protein of claim 1, further comprising a nuclear localization signal (NLS).

6. The fusion protein of claim 1, wherein the fusion protein comprises an artificial transactivation domain (ATAD).

7. The fusion protein of claim 1, further comprising a linker selected from the group consisting of Proline, Glycine, Alanine, Leucine, Glutamic acid, Threonine, and Serine.

8. The fusion protein of claim 1, further comprising at least one end group selected from the group consisting of Alanine and Glycine.

9. The fusion protein of claim 1, said fusion protein comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

10. A composition comprising the fusion protein of claim 1 and at least one stabilizer.

11. The composition of claim 10, wherein the stabilizer is a lipid rich serum.

12. A method for generating induced pluripotent cells, the method comprising the step of:
   a. contacting at least one fusion protein as defined in claim 1 with at least one target cell.

13. The method of claim 12, wherein the step of contacting is carried out for a duration of from 6 hours to 60 days.

14. The method of claim 12, wherein the at least one target cells is selected from the group consisting of embryonic stem cells, adult stem cells, and somatic cells of mammals.

15. The fusion protein of claim 1, wherein the stem cell factor is selected from the group comprising Oct4, Sox2, nanog, klf4, lin28, hTERT, myc, and SV40.

16. The method of claim 14, wherein the cells are derived from at least one of the group consisting of cells of flies, worms, and lower eukaryotes.

17. The method of claim 16, wherein the flies are *D. melanogaster*, the worms are *C. elegans*, and the lower eukaryotes are yeasts.

18. The method of claim 17, wherein the yeasts are *S. cerevisiae*.

* * * * *

```
                               SEQUENCE LISTING

<160> NUMBER OF SEQ ID NOS: 22

<210> SEQ ID NO 1
<211> LENGTH: 395
<212> TYPE: PRT
<213> ORGANISM: Artificial
<220> FEATURE:
<223> OTHER INFORMATION: Fusion protein Oct4NTH

<400> SEQUENCE: 1

Met Asn Ser Pro Arg Ala Gly His Leu Ala Ser Asp Phe Ala Phe Ser
1               5                   10                  15

Pro Pro Pro Gly Gly Gly Asp Gly Ser Ala Gly Leu Glu Pro Gly Trp
            20                  25                  30

Val Asp Pro Arg Thr Trp Leu Ser Phe Gln Gly Pro Pro Gly Gly Pro
        35                  40                  45

Gly Ile Gly Pro Gly Ser Glu Val Leu Gly Ile Ser Pro Cys Pro Pro
    50                  55                  60

Ala Tyr Glu Phe Cys Gly Gly Met Ala Tyr Cys Gly Pro Gln Val Gly
65                  70                  75                  80

Leu Gly Leu Val Pro Gln Val Gly Val Glu Thr Leu Gln Pro Glu Gly
                85                  90                  95

Gln Ala Gly Ala Arg Val Glu Ser Asn Ser Glu Gly Thr Ser Ser Glu
            100                 105                 110

Pro Cys Ala Asp Arg Pro Asn Ala Val Lys Leu Glu Lys Val Glu Pro
        115                 120                 125

Thr Pro Glu Glu Ser Gln Asp Met Lys Ala Leu Gln Lys Glu Leu Glu
    130                 135                 140

Gln Phe Ala Lys Leu Leu Lys Gln Lys Arg Ile Thr Leu Gly Tyr Thr
145                 150                 155                 160

Gln Ala Asp Val Gly Leu Thr Leu Gly Val Leu Phe Gly Lys Val Phe
                165                 170                 175

Ser Gln Thr Thr Ile Cys Arg Phe Glu Ala Leu Gln Leu Ser Leu Lys
```

-continued

```
                       180                 185                 190
Asn Met Cys Lys Leu Arg Pro Leu Glu Lys Trp Val Glu Ala
            195                 200                 205
Asp Asn Asn Glu Asn Leu Gln Glu Ile Cys Lys Ser Glu Thr Leu Val
        210                 215                 220
Gln Ala Arg Lys Arg Lys Arg Thr Ser Ile Glu Asn Arg Val Arg Trp
225                 230                 235                 240
Ser Leu Glu Thr Met Phe Leu Lys Cys Pro Lys Pro Ser Leu Gln Gln
                245                 250                 255
Ile Thr His Ile Ala Asn Gln Leu Gly Leu Glu Lys Asp Val Val Arg
            260                 265                 270
Val Trp Phe Cys Asn Arg Arg Gln Lys Gly Lys Arg Ser Ser Ile Glu
        275                 280                 285
Tyr Ser Gln Arg Glu Glu Tyr Glu Ala Thr Gly Thr Pro Phe Pro Gly
            290                 295                 300
Gly Val Ser Phe Pro Leu Pro Pro Gly Pro His Phe Gly Thr Pro Gly
305                 310                 315                 320
Tyr Gly Ser Pro His Phe Thr Thr Leu Tyr Ser Val Pro Phe Pro Glu
                325                 330                 335
Gly Glu Ala Phe Pro Ser Val Pro Val Thr Ala Leu Gly Ser Pro Met
            340                 345                 350
His Ser Asn Ala Ser Thr Ser Lys Lys Arg Lys Val Thr Ser Ala
355                 360                 365
Ala Ala Gly Arg Lys Lys Arg Arg Gln Arg Arg Pro Pro Ala Ala
        370                 375                 380
Ala Leu Glu His His His His His His His
385                 390                 395

<210> SEQ ID NO 2
<211> LENGTH: 387
<212> TYPE: PRT
<213> ORGANISM: Artificial
<220> FEATURE:
<223> OTHER INFORMATION: Fusion protein Oct4TH

<400> SEQUENCE: 2

Met Asn Ser Pro Arg Ala Gly His Leu Ala Ser Asp Phe Ala Phe Ser
1               5                   10                  15
Pro Pro Pro Gly Gly Gly Asp Gly Ser Ala Gly Leu Glu Pro Gly Trp
                20                  25                  30
Val Asp Pro Arg Thr Trp Leu Ser Phe Gln Gly Pro Pro Gly Gly Pro
            35                  40                  45
Gly Ile Gly Pro Gly Ser Glu Val Leu Gly Ile Ser Pro Cys Pro Pro
        50                  55                  60
Ala Tyr Glu Phe Cys Gly Gly Met Ala Tyr Cys Gly Pro Gln Val Gly
65                  70                  75                  80
Leu Gly Leu Val Pro Gln Val Gly Val Glu Thr Leu Gln Pro Glu Gly
                85                  90                  95
Gln Ala Gly Ala Arg Val Glu Ser Asn Ser Glu Gly Thr Ser Ser Glu
            100                 105                 110
Pro Cys Ala Asp Arg Pro Asn Ala Val Lys Leu Glu Lys Val Glu Pro
        115                 120                 125
Thr Pro Glu Glu Ser Gln Asp Met Lys Ala Leu Gln Lys Glu Leu Glu
    130                 135                 140
Gln Phe Ala Lys Leu Leu Lys Gln Lys Arg Ile Thr Leu Gly Tyr Thr
145                 150                 155                 160
```

Gln Ala Asp Val Gly Leu Thr Leu Gly Val Leu Phe Gly Lys Val Phe
              165                 170                 175

Ser Gln Thr Thr Ile Cys Arg Phe Glu Ala Leu Gln Leu Ser Leu Lys
              180                 185                 190

Asn Met Cys Lys Leu Arg Pro Leu Leu Glu Lys Trp Val Glu Ala
              195                 200                 205

Asp Asn Asn Glu Asn Leu Gln Glu Ile Cys Lys Ser Glu Thr Leu Val
              210                 215                 220

Gln Ala Arg Lys Arg Lys Arg Thr Ser Ile Glu Asn Arg Val Arg Trp
225                 230                 235                 240

Ser Leu Glu Thr Met Phe Leu Lys Cys Pro Lys Pro Ser Leu Gln Gln
              245                 250                 255

Ile Thr His Ile Ala Asn Gln Leu Gly Leu Glu Lys Asp Val Val Arg
              260                 265                 270

Val Trp Phe Cys Asn Arg Arg Gln Lys Gly Lys Arg Ser Ser Ile Glu
              275                 280                 285

Tyr Ser Gln Arg Glu Glu Tyr Glu Ala Thr Gly Thr Pro Phe Pro Gly
              290                 295                 300

Gly Val Ser Phe Pro Leu Pro Pro Gly Pro His Phe Gly Thr Pro Gly
305                 310                 315                 320

Tyr Gly Ser Pro His Phe Thr Thr Leu Tyr Ser Val Pro Phe Pro Glu
              325                 330                 335

Gly Glu Ala Phe Pro Ser Val Pro Val Thr Ala Leu Gly Ser Pro Met
              340                 345                 350

His Ser Asn Ala Ser Thr Ser Ala Ala Ala Gly Arg Lys Lys Arg Arg
              355                 360                 365

Gln Arg Arg Arg Pro Pro Ala Ala Ala Leu Glu His His His His
              370                 375                 380

His His His
385

<210> SEQ ID NO 3
<211> LENGTH: 395
<212> TYPE: PRT
<213> ORGANISM: Artificial
<220> FEATURE:
<223> OTHER INFORMATION: Fusion protein HTNOct4

<400> SEQUENCE: 3

Met Gly His His His His His His Gly Met Gly Ala Ala Gly Arg Lys
1               5                   10                  15

Lys Arg Arg Gln Arg Arg Arg Pro Pro Ala Gly Thr Ser Gly Asn Ser
              20                  25                  30

Lys Lys Lys Arg Lys Val Gly Asn Ser Pro Arg Ala Gly His Leu Ala
              35                  40                  45

Ser Asp Phe Ala Phe Ser Pro Pro Gly Gly Asp Gly Ser Ala
              50                  55                  60

Gly Leu Glu Pro Gly Trp Val Asp Pro Arg Thr Trp Leu Ser Phe Gln
65                  70                  75                  80

Gly Pro Pro Gly Gly Pro Gly Ile Gly Pro Gly Ser Glu Val Leu Gly
              85                  90                  95

Ile Ser Pro Cys Pro Pro Ala Tyr Glu Phe Cys Gly Gly Met Ala Tyr
              100                 105                 110

Cys Gly Pro Gln Val Gly Leu Gly Leu Val Pro Gln Val Gly Val Glu
              115                 120                 125

```
Thr Leu Gln Pro Glu Gly Gln Ala Gly Ala Arg Val Glu Ser Asn Ser
            130                 135                 140

Glu Gly Thr Ser Ser Glu Pro Cys Ala Asp Arg Pro Asn Ala Val Lys
145                 150                 155                 160

Leu Glu Lys Val Glu Pro Thr Pro Glu Glu Ser Gln Asp Met Lys Ala
                165                 170                 175

Leu Gln Lys Glu Leu Glu Gln Phe Ala Lys Leu Leu Lys Gln Lys Arg
            180                 185                 190

Ile Thr Leu Gly Tyr Thr Gln Ala Asp Val Gly Leu Thr Leu Gly Val
        195                 200                 205

Leu Phe Gly Lys Val Phe Ser Gln Thr Thr Ile Cys Arg Phe Glu Ala
    210                 215                 220

Leu Gln Leu Ser Leu Lys Asn Met Cys Lys Leu Arg Pro Leu Leu Glu
225                 230                 235                 240

Lys Trp Val Glu Glu Ala Asp Asn Asn Glu Asn Leu Gln Glu Ile Cys
                245                 250                 255

Lys Ser Glu Thr Leu Val Gln Ala Arg Lys Arg Lys Arg Thr Ser Ile
            260                 265                 270

Glu Asn Arg Val Arg Trp Ser Leu Glu Thr Met Phe Leu Lys Cys Pro
        275                 280                 285

Lys Pro Ser Leu Gln Gln Ile Thr His Ile Ala Asn Gln Leu Gly Leu
    290                 295                 300

Glu Lys Asp Val Val Arg Val Trp Phe Cys Asn Arg Arg Gln Lys Gly
305                 310                 315                 320

Lys Arg Ser Ser Ile Glu Tyr Ser Gln Arg Glu Glu Tyr Glu Ala Thr
                325                 330                 335

Gly Thr Pro Phe Pro Gly Gly Val Ser Phe Pro Leu Pro Gly Pro
            340                 345                 350

His Phe Gly Thr Pro Gly Tyr Gly Ser Pro His Phe Thr Thr Leu Tyr
        355                 360                 365

Ser Val Pro Phe Pro Glu Gly Glu Ala Phe Pro Ser Val Pro Val Thr
    370                 375                 380

Ala Leu Gly Ser Pro Met His Ser Asn Ala Ser
385                 390                 395

<210> SEQ ID NO 4
<211> LENGTH: 386
<212> TYPE: PRT
<213> ORGANISM: Artificial
<220> FEATURE:
<223> OTHER INFORMATION: Fusion protein HTOct4

<400> SEQUENCE: 4

Met Gly His His His His His His Gly Met Gly Ala Ala Gly Arg Lys
1               5                   10                  15

Lys Arg Arg Gln Arg Arg Arg Pro Pro Ala Gly Thr Ser Gly Asn Ser
            20                  25                  30

Pro Arg Ala Gly His Leu Ala Ser Asp Phe Ala Phe Ser Pro Pro Pro
        35                  40                  45

Gly Gly Gly Asp Gly Ser Ala Gly Leu Glu Pro Gly Trp Val Asp Pro
    50                  55                  60

Arg Thr Trp Leu Ser Phe Gln Gly Pro Pro Gly Gly Pro Gly Ile Gly
65                  70                  75                  80

Pro Gly Ser Glu Val Leu Gly Ile Ser Pro Cys Pro Pro Ala Tyr Glu
                85                  90                  95

Phe Cys Gly Gly Met Ala Tyr Cys Gly Pro Gln Val Gly Leu Gly Leu
```

```
                    100                 105                 110
Val Pro Gln Val Gly Val Glu Thr Leu Gln Pro Glu Gly Gln Ala Gly
        115                 120                 125

Ala Arg Val Glu Ser Asn Ser Glu Gly Thr Ser Ser Glu Pro Cys Ala
        130                 135                 140

Asp Arg Pro Asn Ala Val Lys Leu Glu Lys Val Glu Pro Thr Pro Glu
145                 150                 155                 160

Glu Ser Gln Asp Met Lys Ala Leu Gln Lys Glu Leu Glu Gln Phe Ala
                165                 170                 175

Lys Leu Leu Lys Gln Lys Arg Ile Thr Leu Gly Tyr Thr Gln Ala Asp
            180                 185                 190

Val Gly Leu Thr Leu Gly Val Leu Phe Gly Lys Val Phe Ser Gln Thr
        195                 200                 205

Thr Ile Cys Arg Phe Glu Ala Leu Gln Leu Ser Leu Lys Asn Met Cys
    210                 215                 220

Lys Leu Arg Pro Leu Leu Glu Lys Trp Val Glu Glu Ala Asp Asn Asn
225                 230                 235                 240

Glu Asn Leu Gln Glu Ile Cys Lys Ser Glu Thr Leu Val Gln Ala Arg
                245                 250                 255

Lys Arg Lys Arg Thr Ser Ile Glu Asn Arg Val Arg Trp Ser Leu Glu
            260                 265                 270

Thr Met Phe Leu Lys Cys Pro Lys Pro Ser Leu Gln Gln Ile Thr His
        275                 280                 285

Ile Ala Asn Gln Leu Gly Leu Glu Lys Asp Val Val Arg Val Trp Phe
    290                 295                 300

Cys Asn Arg Arg Gln Lys Gly Lys Arg Ser Ser Ile Glu Tyr Ser Gln
305                 310                 315                 320

Arg Glu Glu Tyr Glu Ala Thr Gly Thr Pro Phe Pro Gly Gly Val Ser
                325                 330                 335

Phe Pro Leu Pro Pro Gly Pro His Phe Gly Thr Pro Gly Tyr Gly Ser
            340                 345                 350

Pro His Phe Thr Thr Leu Tyr Ser Val Pro Phe Pro Glu Gly Glu Ala
        355                 360                 365

Phe Pro Ser Val Pro Val Thr Ala Leu Gly Ser Pro Met His Ser Asn
    370                 375                 380

Ala Ser
385

<210> SEQ ID NO 5
<211> LENGTH: 364
<212> TYPE: PRT
<213> ORGANISM: Artificial
<220> FEATURE:
<223> OTHER INFORMATION: Fusion protein Sox2NTH

<400> SEQUENCE: 5

Met Asn Ser Pro Arg Met Tyr Asn Met Met Glu Thr Glu Leu Lys Pro
1               5                   10                  15

Pro Gly Pro Gln Gln Ala Ser Gly Gly Gly Gly Gly Gly Asn Ala
            20                  25                  30

Thr Ala Ala Ala Thr Gly Gly Asn Gln Lys Asn Ser Pro Asp Arg Val
        35                  40                  45

Lys Arg Pro Met Asn Ala Phe Met Val Trp Ser Arg Gly Gln Arg Arg
    50                  55                  60

Lys Met Ala Gln Glu Asn Pro Lys Met His Asn Ser Glu Ile Ser Lys
65                  70                  75                  80
```

```
Arg Leu Gly Ala Glu Trp Lys Leu Leu Ser Glu Thr Glu Lys Arg Pro
                85                  90                  95

Phe Ile Asp Glu Ala Lys Arg Leu Arg Ala Leu His Met Lys Glu His
            100                 105                 110

Pro Asp Tyr Lys Tyr Arg Pro Arg Arg Lys Thr Lys Thr Leu Met Lys
        115                 120                 125

Lys Asp Lys Tyr Thr Leu Pro Gly Gly Leu Leu Ala Pro Gly Gly Asn
130                 135                 140

Ser Met Ala Ser Gly Val Gly Val Gly Ala Gly Leu Gly Ala Gly Val
145                 150                 155                 160

Asn Gln Arg Met Asp Ser Tyr Ala His Met Asn Gly Trp Ser Asn Gly
                165                 170                 175

Ser Tyr Ser Met Met Gln Glu Gln Leu Gly Tyr Pro Gln His Pro Gly
            180                 185                 190

Leu Asn Ala His Gly Ala Ala Gln Met Gln Pro Met His Arg Tyr Asp
        195                 200                 205

Val Ser Ala Leu Gln Tyr Asn Ser Met Thr Ser Ser Gln Thr Tyr Met
210                 215                 220

Asn Gly Ser Pro Thr Tyr Ser Met Ser Tyr Ser Gln Gln Gly Thr Pro
225                 230                 235                 240

Gly Met Ala Leu Gly Ser Met Gly Ser Val Val Lys Ser Glu Ala Ser
                245                 250                 255

Ser Ser Pro Pro Val Val Thr Ser Ser Ser His Ser Arg Ala Pro Cys
            260                 265                 270

Gln Ala Gly Asp Leu Arg Asp Met Ile Ser Met Tyr Leu Pro Gly Ala
        275                 280                 285

Glu Val Pro Glu Pro Ala Ala Pro Ser Arg Leu His Met Ala Gln His
290                 295                 300

Tyr Gln Ser Gly Pro Val Pro Gly Thr Ala Ile Asn Gly Thr Leu Pro
305                 310                 315                 320

Leu Ser His Met Ala Ser Thr Ser Lys Lys Lys Arg Lys Val Thr Ser
                325                 330                 335

Ala Ala Ala Gly Arg Lys Lys Arg Gln Arg Arg Pro Pro Ala
            340                 345                 350

Ala Ala Leu Glu His His His His His His
        355                 360

<210> SEQ ID NO 6
<211> LENGTH: 356
<212> TYPE: PRT
<213> ORGANISM: Artificial
<220> FEATURE:
<223> OTHER INFORMATION: Fusion protein Sox2TH

<400> SEQUENCE: 6

Met Asn Ser Pro Arg Met Tyr Asn Met Met Glu Thr Glu Leu Lys Pro
1               5                   10                  15

Pro Gly Pro Gln Gln Ala Ser Gly Gly Gly Gly Gly Gly Asn Ala
            20                  25                  30

Thr Ala Ala Thr Gly Gly Asn Gln Lys Asn Ser Pro Asp Arg Val
        35                  40                  45

Lys Arg Pro Met Asn Ala Phe Met Val Trp Ser Arg Gly Gln Arg Arg
50                  55                  60

Lys Met Ala Gln Glu Asn Pro Lys Met His Asn Ser Glu Ile Ser Lys
65                  70                  75                  80
```

```
Arg Leu Gly Ala Glu Trp Lys Leu Leu Ser Glu Thr Glu Lys Arg Pro
                85                  90                  95

Phe Ile Asp Glu Ala Lys Arg Leu Arg Ala Leu His Met Lys Glu His
            100                 105                 110

Pro Asp Tyr Lys Tyr Arg Pro Arg Arg Lys Thr Lys Thr Leu Met Lys
        115                 120                 125

Lys Asp Lys Tyr Thr Leu Pro Gly Gly Leu Leu Ala Pro Gly Gly Asn
    130                 135                 140

Ser Met Ala Ser Gly Val Gly Val Gly Ala Gly Leu Gly Ala Gly Val
145                 150                 155                 160

Asn Gln Arg Met Asp Ser Tyr Ala His Met Asn Gly Trp Ser Asn Gly
                165                 170                 175

Ser Tyr Ser Met Met Gln Glu Gln Leu Gly Tyr Pro Gln His Pro Gly
            180                 185                 190

Leu Asn Ala His Gly Ala Ala Gln Met Gln Pro Met His Arg Tyr Asp
        195                 200                 205

Val Ser Ala Leu Gln Tyr Asn Ser Met Thr Ser Ser Gln Thr Tyr Met
    210                 215                 220

Asn Gly Ser Pro Thr Tyr Ser Met Ser Tyr Ser Gln Gln Gly Thr Pro
225                 230                 235                 240

Gly Met Ala Leu Gly Ser Met Gly Ser Val Val Lys Ser Glu Ala Ser
                245                 250                 255

Ser Ser Pro Pro Val Val Thr Ser Ser Ser His Ser Arg Ala Pro Cys
            260                 265                 270

Gln Ala Gly Asp Leu Arg Asp Met Ile Ser Met Tyr Leu Pro Gly Ala
        275                 280                 285

Glu Val Pro Glu Pro Ala Ala Pro Ser Arg Leu His Met Ala Gln His
    290                 295                 300

Tyr Gln Ser Gly Pro Val Pro Gly Thr Ala Ile Asn Gly Thr Leu Pro
305                 310                 315                 320

Leu Ser His Met Ala Ser Thr Ser Ala Ala Ala Gly Arg Lys Lys Arg
                325                 330                 335

Arg Gln Arg Arg Arg Pro Pro Ala Ala Ala Leu Glu His His His His
            340                 345                 350

His His His His
        355

<210> SEQ ID NO 7
<211> LENGTH: 364
<212> TYPE: PRT
<213> ORGANISM: Artificial
<220> FEATURE:
<223> OTHER INFORMATION: Fusion protein HTNSox2

<400> SEQUENCE: 7

Met Gly His His His His His His Gly Met Gly Ala Ala Gly Arg Lys
1               5                   10                  15

Lys Arg Arg Gln Arg Arg Pro Pro Ala Gly Thr Ser Gly Asn Ser
            20                  25                  30

Lys Lys Lys Arg Lys Val Gly Asn Ser Pro Arg Met Tyr Asn Met Met
        35                  40                  45

Glu Thr Glu Leu Lys Pro Pro Gly Pro Gln Gln Ala Ser Gly Gly Gly
    50                  55                  60

Gly Gly Gly Gly Asn Ala Thr Ala Ala Ala Thr Gly Gly Asn Gln Lys
65                  70                  75                  80

Asn Ser Pro Asp Arg Val Lys Arg Pro Met Asn Ala Phe Met Val Trp
```

```
                    85                  90                  95
Ser Arg Gly Gln Arg Arg Lys Met Ala Gln Glu Asn Pro Lys Met His
                100                 105                 110

Asn Ser Glu Ile Ser Lys Arg Leu Gly Ala Glu Trp Lys Leu Leu Ser
            115                 120                 125

Glu Thr Glu Lys Arg Pro Phe Ile Asp Glu Ala Lys Arg Leu Arg Ala
        130                 135                 140

Leu His Met Lys Glu His Pro Asp Tyr Lys Tyr Arg Pro Arg Arg Lys
145                 150                 155                 160

Thr Lys Thr Leu Met Lys Lys Asp Lys Tyr Thr Leu Pro Gly Gly Leu
                165                 170                 175

Leu Ala Pro Gly Gly Asn Ser Met Ala Ser Gly Val Gly Val Gly Ala
            180                 185                 190

Gly Leu Gly Ala Gly Val Asn Gln Arg Met Asp Ser Tyr Ala His Met
        195                 200                 205

Asn Gly Trp Ser Asn Gly Ser Tyr Ser Met Met Gln Glu Gln Leu Gly
    210                 215                 220

Tyr Pro Gln His Pro Gly Leu Asn Ala His Gly Ala Ala Gln Met Gln
225                 230                 235                 240

Pro Met His Arg Tyr Asp Val Ser Ala Leu Gln Tyr Asn Ser Met Thr
                245                 250                 255

Ser Ser Gln Thr Tyr Met Asn Gly Ser Pro Thr Tyr Ser Met Ser Tyr
            260                 265                 270

Ser Gln Gln Gly Thr Pro Gly Met Ala Leu Gly Ser Met Gly Ser Val
        275                 280                 285

Val Lys Ser Glu Ala Ser Ser Ser Pro Pro Val Val Thr Ser Ser Ser
290                 295                 300

His Ser Arg Ala Pro Cys Gln Ala Gly Asp Leu Arg Asp Met Ile Ser
305                 310                 315                 320

Met Tyr Leu Pro Gly Ala Glu Val Pro Glu Pro Ala Ala Pro Ser Arg
                325                 330                 335

Leu His Met Ala Gln His Tyr Gln Ser Gly Pro Val Pro Gly Thr Ala
            340                 345                 350

Ile Asn Gly Thr Leu Pro Leu Ser His Met Ala Ser
        355                 360

<210> SEQ ID NO 8
<211> LENGTH: 355
<212> TYPE: PRT
<213> ORGANISM: Artificial
<220> FEATURE:
<223> OTHER INFORMATION: Fusion protein HTSox2

<400> SEQUENCE: 8

Met Gly His His His His His His Gly Met Gly Ala Ala Gly Arg Lys
1               5                   10                  15

Lys Arg Arg Gln Arg Arg Pro Pro Ala Gly Thr Ser Gly Asn Ser
            20                  25                  30

Pro Arg Met Tyr Asn Met Met Glu Thr Glu Leu Lys Pro Pro Gly Pro
        35                  40                  45

Gln Gln Ala Ser Gly Gly Gly Gly Gly Gly Asn Ala Thr Ala Ala
    50                  55                  60

Ala Thr Gly Gly Asn Gln Lys Asn Ser Pro Asp Arg Val Lys Arg Pro
65                  70                  75                  80

Met Asn Ala Phe Met Val Trp Ser Arg Gly Gln Arg Arg Lys Met Ala
                85                  90                  95
```

-continued

```
Gln Glu Asn Pro Lys Met His Asn Ser Glu Ile Ser Lys Arg Leu Gly
            100                 105                 110
Ala Glu Trp Lys Leu Leu Ser Glu Thr Glu Lys Arg Pro Phe Ile Asp
        115                 120                 125
Glu Ala Lys Arg Leu Arg Ala Leu His Met Lys Glu His Pro Asp Tyr
    130                 135                 140
Lys Tyr Arg Pro Arg Arg Lys Thr Lys Thr Leu Met Lys Lys Asp Lys
145                 150                 155                 160
Tyr Thr Leu Pro Gly Gly Leu Leu Ala Pro Gly Gly Asn Ser Met Ala
                165                 170                 175
Ser Gly Val Gly Val Gly Ala Gly Leu Gly Ala Gly Val Asn Gln Arg
            180                 185                 190
Met Asp Ser Tyr Ala His Met Asn Gly Trp Ser Asn Gly Ser Tyr Ser
        195                 200                 205
Met Met Gln Glu Gln Leu Gly Tyr Pro Gln His Pro Gly Leu Asn Ala
    210                 215                 220
His Gly Ala Ala Gln Met Gln Pro Met His Arg Tyr Asp Val Ser Ala
225                 230                 235                 240
Leu Gln Tyr Asn Ser Met Thr Ser Ser Gln Thr Tyr Met Asn Gly Ser
                245                 250                 255
Pro Thr Tyr Ser Met Ser Tyr Ser Gln Gln Gly Thr Pro Gly Met Ala
            260                 265                 270
Leu Gly Ser Met Gly Ser Val Val Lys Ser Glu Ala Ser Ser Ser Pro
        275                 280                 285
Pro Val Val Thr Ser Ser Ser His Ser Arg Ala Pro Cys Gln Ala Gly
    290                 295                 300
Asp Leu Arg Asp Met Ile Ser Met Tyr Leu Pro Gly Ala Glu Val Pro
305                 310                 315                 320
Glu Pro Ala Ala Pro Ser Arg Leu His Met Ala Gln His Tyr Gln Ser
                325                 330                 335
Gly Pro Val Pro Gly Thr Ala Ile Asn Gly Thr Leu Pro Leu Ser His
            340                 345                 350
Met Ala Ser
        355

<210> SEQ ID NO 9
<211> LENGTH: 20
<212> TYPE: DNA
<213> ORGANISM: Artificial
<220> FEATURE:
<223> OTHER INFORMATION: PCR primer b-Actin_forw

<400> SEQUENCE: 9
ctggctccta gcaccatgaa                                              20

<210> SEQ ID NO 10
<211> LENGTH: 20
<212> TYPE: DNA
<213> ORGANISM: Artificial
<220> FEATURE:
<223> OTHER INFORMATION: PCR primer b-Actin_rev

<400> SEQUENCE: 10
gccggactca tcgtactcct                                              20

<210> SEQ ID NO 11
<211> LENGTH: 21
<212> TYPE: DNA
```

```
<213> ORGANISM: Artificial
<220> FEATURE:
<223> OTHER INFORMATION: PCR primer Pou5f1_for

<400> SEQUENCE: 11
ccctgcagaa ggagctagaa c                                                    21

<210> SEQ ID NO 12
<211> LENGTH: 20
<212> TYPE: DNA
<213> ORGANISM: Artificial
<220> FEATURE:
<223> OTHER INFORMATION: PCR primer Pou5f1_rev

<400> SEQUENCE: 12
cttaaggctg agctgcaagg                                                      20

<210> SEQ ID NO 13
<211> LENGTH: 25
<212> TYPE: DNA
<213> ORGANISM: Artificial
<220> FEATURE:
<223> OTHER INFORMATION: PCR primer Sox2_forw

<400> SEQUENCE: 13 cccctttat tttccgtagt tgtat                                                 25

<210> SEQ ID NO 14
<211> LENGTH: 25
<212> TYPE: DNA
<213> ORGANISM: Artificial
<220> FEATURE:
<223> OTHER INFORMATION: PCR primer Sox2_rev

<400> SEQUENCE: 14
tcaaactgtg cataatggag taaaa                                                25

<210> SEQ ID NO 15
<211> LENGTH: 24
<212> TYPE: DNA
<213> ORGANISM: Artificial
<220> FEATURE:
<223> OTHER INFORMATION: PCR primer Nanog_for

<400> SEQUENCE: 15
agggtctgct actgagatgc tctg                                                 24

<210> SEQ ID NO 16
<211> LENGTH: 24
<212> TYPE: DNA
<213> ORGANISM: Artificial
<220> FEATURE:
<223> OTHER INFORMATION: PCR primer Nanog_rev

<400> SEQUENCE: 16
caaccactgg tttttctgcc accg                                                 24

<210> SEQ ID NO 17
<211> LENGTH: 131
<212> TYPE: DNA
<213> ORGANISM: Artificial
<220> FEATURE:
<223> OTHER INFORMATION: Excerpt of coding region of vector pSESAME-N
```

<400> SEQUENCE: 17
ccatgggcca tcaccatcac catcacggca tgggcgctgc aggtcgcaag aaacgtcgcc     60
aacgtcgccg tccgcctgca ggcactagtg ggaattctaa gaagaagagg aaggtgggga    120
attctcctag g    131

<210> SEQ ID NO 18
<211> LENGTH: 126
<212> TYPE: DNA
<213> ORGANISM: Artificial
<220> FEATURE:
<223> OTHER INFORMATION: Excerpt of coding region of vector pSESAME-C

<400> SEQUENCE: 18
gctagcacta gtaagaagaa gaggaaggtg actagtgcgg ccgcgggtcg caagaaacgt     60
cgccaacgtc gccgtccgcc tgcggccgcg ctcgagcacc accatcacca tcaccatcac    120
taagtg    126

<210> SEQ ID NO 19
<211> LENGTH: 6
<212> TYPE: PRT
<213> ORGANISM: Artificial
<220> FEATURE:
<223> OTHER INFORMATION: nuclear localisation signal

<400> SEQUENCE: 19

Lys Lys Lys Arg Lys Val
1               5

<210> SEQ ID NO 20
<211> LENGTH: 18
<212> TYPE: DNA
<213> ORGANISM: Artificial
<220> FEATURE:
<223> OTHER INFORMATION: coding sequence for nuclear localisation signal

<400> SEQUENCE: 20
aagaagaaga ggaaggtg    18

<210> SEQ ID NO 21
<211> LENGTH: 12
<212> TYPE: PRT
<213> ORGANISM: Artificial
<220> FEATURE:
<223> OTHER INFORMATION: basic peptide of HIV-1 TAT

<400> SEQUENCE: 21

Gly Arg Lys Lys Arg Arg Gln Arg Arg Arg Pro Pro
1               5                   10

<210> SEQ ID NO 22
<211> LENGTH: 36
<212> TYPE: DNA
<213> ORGANISM: Artificial
<220> FEATURE:
<223> OTHER INFORMATION: coding sequence for basic TAT peptide

<400> SEQUENCE: 22
ggtcgcaaga aacgtcgcca acgtcgccgt ccgcct    36